US010001497B2

(12) United States Patent
Ochranek et al.

(10) Patent No.: US 10,001,497 B2
(45) Date of Patent: Jun. 19, 2018

(54) DIAGNOSTIC ANALYZERS WITH PRETREATMENT CAROUSELS AND RELATED METHODS

(71) Applicant: Abbott Laboratories, Abbott Park, IL (US)

(72) Inventors: Brian L. Ochranek, Southlake, TX (US); David C. Arnquist, The Colony, TX (US)

(73) Assignee: ABBOTT LABORATORIES, Abbott Park, IL (US)

( * ) Notice: Subject to any disclaimer, the term of this patent is extended or adjusted under 35 U.S.C. 154(b) by 120 days.

(21) Appl. No.: 14/142,474

(22) Filed: Dec. 27, 2013

(65) Prior Publication Data
US 2014/0273241 A1    Sep. 18, 2014

Related U.S. Application Data

(60) Provisional application No. 61/792,779, filed on Mar. 15, 2013.

(51) Int. Cl.
*G01N 35/00* (2006.01)
*G01N 35/02* (2006.01)
*G01N 35/04* (2006.01)

(52) U.S. Cl.
CPC .......... *G01N 35/025* (2013.01); *G01N 35/04* (2013.01); *G01N 2035/0455* (2013.01);
(Continued)

(58) Field of Classification Search
None
See application file for complete search history.

(56) References Cited

U.S. PATENT DOCUMENTS 3,449,959 A  6/1969 Grimshaw
3,451,433 A  6/1969 Cunningham et al.
(Continued)

FOREIGN PATENT DOCUMENTS

CN    102520200    6/2012
DE  112010001896    6/2012
(Continued)

OTHER PUBLICATIONS

International Search Report and Written Opinion, issued by the International Searching Authority in connection with International patent application No. PCT/US2013/078041, dated Sep. 19, 2014, 16 pages.
(Continued)

*Primary Examiner* — Xiaoyun R Xu
(74) *Attorney, Agent, or Firm* — Hanley, Flight & Zimmerman, LLC

(57) ABSTRACT

Diagnostic analyzers with pretreatment carousels and related methods are disclosed. An example apparatus includes a first carousel that includes a first annular array of slots to receive a first vessel. The example first carousel also includes a first track of rotation about the first carousel having a first diameter and a second track of rotation about the first carousel having a second diameter smaller than the first diameter. The example apparatus includes a first diverter to move the first vessel from the first track to the second track. In addition, the example apparatus includes a second carousel coaxial with the first carousel. The example second carousel includes a second annular array of slots to receive a second vessel.

45 Claims, 15 Drawing Sheets

(52) U.S. Cl.
CPC ............... *G01N 2035/0456* (2013.01); *G01N 2035/0465* (2013.01); *G01N 2035/0467* (2013.01); *Y10T 436/111666* (2015.01)

(56) References Cited

U.S. PATENT DOCUMENTS

| | | |
|---|---|---|
| 3,484,206 A | 12/1969 | Loebl |
| 4,738,825 A | 4/1988 | Kelln et al. |
| 4,774,055 A | 9/1988 | Wakatake et al. |
| 4,808,380 A | 2/1989 | Minekane |
| 4,848,917 A | 7/1989 | Benin et al. |
| 4,849,177 A | 7/1989 | Jordan |
| 4,906,433 A | 3/1990 | Minekane |
| 5,037,612 A | 8/1991 | Takahashi |
| 5,051,238 A | 9/1991 | Umetsu et al. |
| 5,071,625 A | 12/1991 | Kelln et al. |
| 5,077,013 A | 12/1991 | Guigan |
| 5,154,896 A | 10/1992 | Mochida et al. |
| 5,244,633 A | 9/1993 | Jakubowicz et al. |
| 5,250,440 A | 10/1993 | Kelln et al. |
| 5,266,268 A | 11/1993 | Antocci et al. |
| 5,270,212 A | 12/1993 | Horiuchi et al. |
| 5,311,426 A | 5/1994 | Donohue et al. |
| 5,314,825 A | 5/1994 | Weyrauch et al. |
| 5,352,612 A | 10/1994 | Huber et al. |
| 5,358,691 A | 10/1994 | Clark et al. |
| 5,360,597 A | 11/1994 | Jakubowicz et al. |
| 5,419,871 A | 5/1995 | Muszak et al. |
| 5,422,271 A | 6/1995 | Chen et al. |
| 5,424,036 A | 6/1995 | Ushikubo |
| 5,424,212 A | 6/1995 | Pinsl-Ober et al. |
| 5,434,083 A | 6/1995 | Mitsumaki et al. |
| 5,439,646 A | 8/1995 | Tanimizu et al. |
| 5,443,791 A | 8/1995 | Cathcart et al. |
| 5,445,794 A | 8/1995 | Wihlborg |
| 5,447,687 A | 9/1995 | Lewis et al. |
| 5,455,175 A | 10/1995 | Wittwer et al. |
| 5,460,780 A | 10/1995 | Devaney, Jr. et al. |
| 5,460,968 A | 10/1995 | Yoshida et al. |
| 5,462,715 A | 10/1995 | Koch et al. |
| 5,466,574 A | 11/1995 | Liberti et al. |
| 5,470,744 A | 11/1995 | Astle |
| 5,482,834 A | 1/1996 | Gillespie |
| 5,482,839 A | 1/1996 | Ashihara et al. |
| 5,482,861 A | 1/1996 | Clark et al. |
| 5,518,693 A | 5/1996 | Tomasso |
| 5,525,300 A | 6/1996 | Danssaert et al. |
| 5,527,673 A | 6/1996 | Reinhartz et al. |
| 5,536,475 A | 7/1996 | Moubayed et al. |
| 5,536,481 A | 7/1996 | Mabire et al. |
| 5,538,849 A | 7/1996 | Uematsu et al. |
| 5,538,976 A | 7/1996 | Okada et al. |
| 5,548,826 A | 8/1996 | Sayers |
| 5,558,839 A | 9/1996 | Matte et al. |
| 5,559,002 A | 9/1996 | Uzan et al. |
| 5,567,595 A | 10/1996 | Kok |
| 5,571,325 A | 11/1996 | Ueyama et al. |
| 5,571,481 A | 11/1996 | Powell et al. |
| 5,575,976 A | 11/1996 | Choperena et al. |
| 5,576,215 A | 11/1996 | Burns et al. |
| 5,578,269 A | 11/1996 | Yaremko et al. |
| 5,578,270 A | 11/1996 | Reichler et al. |
| 5,580,524 A | 12/1996 | Forrest et al. |
| 5,582,796 A | 12/1996 | Carey et al. |
| 5,585,068 A | 12/1996 | Panetz et al. |
| 5,587,129 A | 12/1996 | Kurosaki et al. |
| 5,589,137 A | 12/1996 | Markin et al. |
| 5,595,707 A | 1/1997 | Copeland et al. |
| 5,599,501 A | 2/1997 | Carey et al. |
| 5,611,994 A | 3/1997 | Bailey et al. |
| 5,620,898 A | 4/1997 | Yaremko et al. |
| 5,632,399 A | 5/1997 | Palmieri et al. |
| 5,637,275 A | 6/1997 | Carey et al. |
| 5,639,425 A | 6/1997 | Komiyama et al. |
| 5,650,327 A | 7/1997 | Copeland et al. |
| 5,653,940 A | 8/1997 | Carey et al. |
| 5,654,199 A | 8/1997 | Copeland et al. |
| 5,654,200 A | 8/1997 | Copeland et al. |
| 5,656,493 A | 8/1997 | Mullis et al. |
| 5,658,532 A | 8/1997 | Kurosaki et al. |
| 5,658,799 A | 8/1997 | Choperena et al. |
| 5,670,114 A | 9/1997 | Sakazume et al. |
| 5,670,120 A | 9/1997 | Degenhardt et al. |
| 5,670,375 A | 9/1997 | Seaton et al. |
| 5,677,188 A | 10/1997 | Mitsumaki et al. |
| 5,679,309 A | 10/1997 | Bell |
| 5,681,530 A | 10/1997 | Kuster et al. |
| 5,682,026 A | 10/1997 | Auclair et al. |
| 5,686,046 A | 11/1997 | Malek et al. |
| 5,693,292 A | 12/1997 | Choperena et al. |
| 5,698,450 A | 12/1997 | Ringrose |
| 5,702,950 A | 12/1997 | Tajima |
| 5,705,062 A | 1/1998 | Knobel |
| 5,714,380 A | 2/1998 | Neri et al. |
| 5,716,583 A | 2/1998 | Smethers et al. |
| 5,717,148 A | 2/1998 | Ely et al. |
| 5,720,377 A | 2/1998 | Lapeus et al. |
| 5,720,923 A | 2/1998 | Haff et al. |
| 5,721,141 A | 2/1998 | Babson et al. |
| 5,723,092 A | 3/1998 | Babson et al. |
| 5,730,938 A | 3/1998 | Carbonari et al. |
| 5,730,939 A | 3/1998 | Kurumada et al. |
| 5,736,101 A | 4/1998 | Gianino |
| 5,736,105 A | 4/1998 | Astle |
| 5,736,413 A | 4/1998 | Uzan et al. |
| 5,738,827 A | 4/1998 | Marquiss |
| 5,741,461 A | 4/1998 | Takahashi et al. |
| 5,741,708 A | 4/1998 | Carey et al. |
| 5,746,977 A | 5/1998 | Imai et al. |
| 5,746,978 A | 5/1998 | Bienhaus et al. |
| 5,748,978 A | 5/1998 | Narayan et al. |
| 5,750,338 A | 5/1998 | Collins et al. |
| 5,762,872 A | 6/1998 | Bühler et al. |
| 5,762,873 A | 6/1998 | Fanning |
| 5,773,268 A | 6/1998 | Korenberg et al. |
| 5,773,296 A | 6/1998 | Montalbano et al. |
| 5,773,662 A | 6/1998 | Imai et al. |
| 5,779,981 A | 7/1998 | Danssaert et al. |
| 5,786,182 A | 7/1998 | Catanzariti et al. |
| 5,789,252 A | 8/1998 | Fujita et al. |
| 5,795,547 A | 8/1998 | Moser et al. |
| 5,795,784 A | 8/1998 | Arnquist et al. |
| 5,807,523 A | 9/1998 | Watts et al. |
| 5,814,277 A | 9/1998 | Bell et al. |
| 5,816,998 A | 10/1998 | Silverstolpe et al. |
| 5,826,129 A | 10/1998 | Hasebe et al. |
| 5,827,478 A | 10/1998 | Carey et al. |
| 5,827,479 A | 10/1998 | Yamazaki et al. |
| 5,827,653 A | 10/1998 | Sammes et al. |
| 5,837,195 A | 11/1998 | Malek et al. |
| 5,843,376 A | 12/1998 | Ishihara et al. |
| 5,846,491 A | 12/1998 | Choperena et al. |
| 5,849,247 A | 12/1998 | Uzan et al. |
| 5,855,847 A | 1/1999 | Oonuma et al. |
| 5,856,194 A | 1/1999 | Arnquist et al. |
| 5,863,506 A | 1/1999 | Farren |
| 5,876,668 A | 3/1999 | Kawashima et al. |
| 5,876,670 A | 3/1999 | Mitsumaki et al. |
| 5,882,594 A | 3/1999 | Kawaguchi et al. |
| 5,882,596 A | 3/1999 | Breeser et al. |
| 5,882,918 A | 3/1999 | Goffe |
| 5,885,353 A | 3/1999 | Strodtbeck et al. |
| 5,885,529 A | 3/1999 | Babson et al. |
| 5,885,530 A | 3/1999 | Babson et al. |
| 5,888,454 A | 3/1999 | Leistner et al. |
| 5,897,783 A | 4/1999 | Howe et al. |
| 5,902,549 A | 5/1999 | Mimura et al. |
| 5,919,622 A | 7/1999 | Macho et al. |
| 5,928,952 A | 7/1999 | Hutchins et al. |
| 5,935,522 A | 8/1999 | Swerdlow et al. |
| 5,948,691 A | 9/1999 | Ekiriwang et al. |
| 5,955,373 A | 9/1999 | Hutchins et al. |
| 5,958,763 A | 9/1999 | Goffe |
| 5,972,295 A | 10/1999 | Hanawa et al. |

(56) References Cited

U.S. PATENT DOCUMENTS

| | | |
|---|---|---|
| 5,985,215 A | 11/1999 | Sakazume et al. |
| 5,985,670 A | 11/1999 | Markin |
| 5,985,671 A | 11/1999 | Leistner et al. |
| 5,985,672 A | 11/1999 | Kegelman et al. |
| 5,988,869 A | 11/1999 | Davidson et al. |
| 6,019,945 A | 2/2000 | Ohishi et al. |
| 6,027,691 A | 2/2000 | Watts et al. |
| 6,033,574 A | 3/2000 | Siddiqi |
| 6,033,880 A | 3/2000 | Haff et al. |
| 6,042,786 A | 3/2000 | Oonuma et al. |
| 6,043,880 A | 3/2000 | Andrews et al. |
| 6,051,101 A | 4/2000 | Ohtani et al. |
| 6,056,923 A | 5/2000 | Diamond et al. |
| 6,060,022 A | 5/2000 | Pang et al. |
| 6,063,340 A | 5/2000 | Lewis et al. |
| 6,068,393 A | 5/2000 | Hutchins et al. |
| 6,068,978 A | 5/2000 | Zaun et al. |
| 6,071,395 A | 6/2000 | Lange |
| 6,071,477 A | 6/2000 | Auclair et al. |
| 6,074,615 A | 6/2000 | Lewis et al. |
| 6,080,364 A | 6/2000 | Mimura et al. |
| 6,086,827 A | 7/2000 | Horner et al. |
| 6,096,272 A | 8/2000 | Clark et al. |
| 6,103,193 A | 8/2000 | Iwahashi et al. |
| 6,106,781 A | 8/2000 | Rosenberg |
| 6,110,676 A | 8/2000 | Coull et al. |
| 6,110,678 A | 8/2000 | Weisburg et al. |
| 6,117,392 A | 9/2000 | Hanawa et al. |
| 6,117,398 A | 9/2000 | Bienhaus et al. |
| 6,117,683 A | 9/2000 | Kodama et al. |
| 6,143,578 A | 11/2000 | Bendele et al. |
| 6,146,592 A | 11/2000 | Kawashima et al. |
| 6,156,565 A | 12/2000 | Maes et al. |
| 6,165,778 A | 12/2000 | Kedar |
| 6,174,670 B1 | 1/2001 | Wittwer |
| 6,232,079 B1 | 5/2001 | Wittwer |
| 6,245,514 B1 | 6/2001 | Wittwer |
| 6,261,521 B1 | 7/2001 | Mimura et al. |
| 6,267,927 B1 | 7/2001 | Pomar Longedo et al. |
| 6,277,332 B1 | 8/2001 | Sucholeiki |
| 6,293,750 B1 | 9/2001 | Cohen et al. |
| 6,299,567 B1 | 10/2001 | Forrest et al. |
| 6,300,068 B1 | 10/2001 | Burg et al. |
| 6,300,138 B1 | 10/2001 | Gleason |
| 6,319,718 B1 | 11/2001 | Matsubara et al. |
| 6,332,636 B1 | 12/2001 | Cohen et al. |
| 6,335,166 B1 | 1/2002 | Ammann et al. |
| 6,337,050 B1 | 1/2002 | Takahashi et al. |
| 6,352,861 B1 | 3/2002 | Copeland et al. |
| 6,374,982 B1 | 4/2002 | Cohen et al. |
| 6,375,898 B1 | 4/2002 | Ulrich |
| 6,377,342 B1 | 4/2002 | Coeurveille |
| 6,386,749 B1 | 5/2002 | Watts et al. |
| 6,399,952 B1 | 6/2002 | Maher et al. |
| 6,436,349 B1 | 8/2002 | Carey et al. |
| 6,444,171 B1 | 9/2002 | Sakazume et al. |
| 6,455,325 B1 | 9/2002 | Tajima |
| 6,461,570 B2 | 10/2002 | Ishihara |
| 6,472,217 B1 | 10/2002 | Richards et al. |
| 6,498,037 B1 | 12/2002 | Carey et al. |
| 6,503,751 B2 | 1/2003 | Hugh |
| 6,509,193 B1 | 1/2003 | Tajima |
| 6,517,782 B1 | 2/2003 | Horner et al. |
| 6,517,783 B2 | 2/2003 | Horner et al. |
| 6,521,183 B1 | 2/2003 | Burri et al. |
| 6,522,976 B2 | 2/2003 | Shiba et al. |
| 6,551,833 B1 | 4/2003 | Lehtinen et al. |
| 6,562,298 B1 | 5/2003 | Arnquist et al. |
| 6,569,627 B2 | 5/2003 | Wittwer et al. |
| 6,579,717 B1 | 6/2003 | Matsubara et al. |
| 6,586,234 B1 | 7/2003 | Burg et al. |
| 6,592,818 B2 | 7/2003 | Ishihara et al. |
| 6,597,450 B1 | 7/2003 | Andrews et al. |
| 6,599,749 B1 | 7/2003 | Kodama et al. |
| 6,605,213 B1 | 8/2003 | Ammann et al. |
| 6,632,654 B1 | 10/2003 | Gebrian et al. |
| 6,709,634 B1 | 3/2004 | Okada et al. |
| 6,723,288 B2 | 4/2004 | Devlin, Sr. et al. |
| 6,733,728 B1 | 5/2004 | Mimura et al. |
| 6,752,967 B2 | 6/2004 | Farina et al. |
| 6,764,649 B2 | 7/2004 | Ammann |
| 6,764,650 B2 | 7/2004 | Takahashi et al. |
| 6,776,961 B2 | 8/2004 | Lindsey et al. |
| 6,780,617 B2 | 8/2004 | Chen |
| 6,787,338 B2 | 9/2004 | Wittwer et al. |
| 6,825,921 B1 | 11/2004 | Modlin et al. |
| 6,827,901 B2 | 12/2004 | Copeland et al. |
| 6,866,821 B2 | 3/2005 | Friedlander et al. |
| 6,878,343 B2 | 4/2005 | Sklar et al. |
| 6,890,742 B2 | 5/2005 | Ammann et al. |
| 6,911,327 B2 | 6/2005 | McMillan et al. |
| 6,919,058 B2 | 7/2005 | Andersson et al. |
| 6,919,175 B1 | 7/2005 | Bienhaus et al. |
| 6,924,152 B2 | 8/2005 | Matsubara et al. |
| 6,943,029 B2 | 9/2005 | Coepland et al. |
| 6,958,130 B1 | 10/2005 | Gicquel et al. |
| 7,011,792 B2 | 3/2006 | Mimura et al. |
| 7,028,831 B2 | 4/2006 | Veiner |
| 7,029,922 B2 | 4/2006 | Miller |
| 7,033,820 B2 | 4/2006 | Ammann |
| 7,081,226 B1 | 7/2006 | Wittwer et al. |
| 7,105,351 B2 | 9/2006 | Matsubara et al. |
| 7,115,090 B2 | 10/2006 | Lagarde |
| 7,115,384 B2 | 10/2006 | Clark et al. |
| 7,118,892 B2 | 10/2006 | Ammann et al. |
| 7,118,918 B2 | 10/2006 | Copeland et al. |
| 7,118,982 B2 | 10/2006 | Govyadinov et al. |
| 7,132,082 B2 | 11/2006 | Aviles et al. |
| 7,135,145 B2 | 11/2006 | Ammann et al. |
| 7,138,091 B2 | 11/2006 | Lee et al. |
| 7,141,213 B1 | 11/2006 | Pang et al. |
| 7,160,998 B2 | 1/2007 | Wittwer et al. |
| 7,169,356 B2 | 1/2007 | Gebrian et al. |
| 7,171,863 B2 | 2/2007 | Tamura et al. |
| 7,182,912 B2 | 2/2007 | Carey et al. |
| 7,217,513 B2 | 5/2007 | Parameswaran et al. |
| 7,220,589 B2 | 5/2007 | Richards et al. |
| 7,250,303 B2 | 7/2007 | Jakubowicz et al. |
| 7,264,111 B2 | 9/2007 | Veiner |
| 7,267,795 B2 | 9/2007 | Ammann et al. |
| 7,270,783 B2 | 9/2007 | Takase et al. |
| 7,273,749 B1 | 9/2007 | Wittwer et al. |
| 7,276,208 B2 | 10/2007 | Sevigny |
| 7,303,139 B1 | 12/2007 | Rudloff |
| 7,331,474 B2 | 2/2008 | Veiner et al. |
| 7,341,691 B2 | 3/2008 | Tamura et al. |
| 7,360,984 B1 | 4/2008 | Sugiyama et al. |
| 7,361,305 B2 | 4/2008 | Mimura et al. |
| 7,381,370 B2 | 6/2008 | Chow et al. |
| 7,384,600 B2 | 6/2008 | Burns et al. |
| 7,390,458 B2 | 6/2008 | Burow et al. |
| 7,396,509 B2 | 7/2008 | Burns |
| 7,402,281 B2 | 7/2008 | Huynh-Ba et al. |
| 7,407,627 B1 | 8/2008 | Rosenberg et al. |
| 7,482,143 B2 | 1/2009 | Ammann et al. |
| 7,524,652 B2 | 4/2009 | Ammann et al. |
| 7,560,255 B2 | 7/2009 | Ammann et al. |
| 7,560,256 B2 | 7/2009 | Ammann et al. |
| 7,575,937 B2 | 8/2009 | Wiggli et al. |
| 7,611,675 B2 | 11/2009 | Sevigny et al. |
| 7,622,078 B2 | 11/2009 | Pagés Pinyol |
| 7,638,337 B2 | 12/2009 | Ammann et al. |
| 7,641,855 B2 | 1/2010 | Farina et al. |
| 7,666,602 B2 | 2/2010 | Ammann et al. |
| 7,666,681 B2 | 2/2010 | Ammann et al. |
| 7,670,553 B2 | 3/2010 | Babson |
| 7,670,554 B2 | 3/2010 | Chow et al. |
| 7,670,832 B2 | 3/2010 | Wittwer et al. |
| 7,700,042 B2 | 4/2010 | Matsumoto et al. |
| 7,700,043 B2 | 4/2010 | Mimura et al. |
| 7,731,414 B2 | 6/2010 | Vincent et al. |
| 7,731,898 B2 | 6/2010 | Burkhardt et al. |
| 7,745,205 B2 | 6/2010 | Wittwer et al. |
| 7,749,441 B2 | 7/2010 | Hanawa et al. |

(56) References Cited

U.S. PATENT DOCUMENTS

| | | |
|---|---|---|
| 7,785,534 B2 | 8/2010 | Watari et al. |
| 7,815,858 B2 | 10/2010 | Sevigny et al. |
| 7,827,874 B2 | 11/2010 | Tsujimura et al. |
| 7,837,452 B2 | 11/2010 | Ignatiev et al. |
| 7,842,237 B1 | 11/2010 | Shibuya et al. |
| 7,842,504 B2 | 11/2010 | Devlin, Sr. |
| 7,850,914 B2 | 12/2010 | Veiner et al. |
| 7,854,892 B2 | 12/2010 | Veiner et al. |
| 7,855,084 B2 | 12/2010 | Jakubowicz et al. |
| 7,858,032 B2 | 12/2010 | Le Comte et al. |
| 7,867,777 B2 | 1/2011 | Aviles et al. |
| 7,910,294 B2 | 3/2011 | Karlsen |
| 7,939,036 B2 | 5/2011 | Burkhardt et al. |
| 7,941,904 B2 | 5/2011 | Smith |
| 7,943,100 B2 | 5/2011 | Rousseau |
| 7,947,225 B2 | 5/2011 | Itoh |
| 7,951,329 B2 | 5/2011 | Malyarov et al. |
| 7,964,140 B2 | 6/2011 | Watari |
| 7,985,375 B2 | 7/2011 | Edens et al. |
| 7,998,409 B2 | 8/2011 | Veiner et al. |
| 7,998,432 B2 | 8/2011 | Rousseau |
| 7,998,751 B2 | 8/2011 | Evers et al. |
| 8,003,050 B2 | 8/2011 | Burkhardt et al. |
| 8,012,419 B2 | 9/2011 | Ammann et al. |
| 8,038,941 B2 | 10/2011 | Devlin, Sr. |
| 8,038,942 B2 | 10/2011 | Pang et al. |
| 8,047,086 B2 | 11/2011 | Smith |
| 8,066,943 B2 | 11/2011 | Kegelman et al. |
| 8,071,053 B2 | 12/2011 | Matsuzaki et al. |
| 8,097,211 B2 | 1/2012 | Hamada et al. |
| 8,114,351 B2 | 2/2012 | Degenhardt et al. |
| 8,119,080 B2 | 2/2012 | Wiggli et al. |
| 8,137,620 B2 | 3/2012 | Ammann et al. |
| 8,142,740 B2 | 3/2012 | Self et al. |
| 8,147,777 B2 | 4/2012 | Schacher et al. |
| 8,153,061 B2 | 4/2012 | Walters |
| 8,154,899 B2 | 4/2012 | Degroot |
| 8,158,058 B2 | 4/2012 | Shiba et al. |
| 8,161,831 B2 | 4/2012 | Fukuma |
| 8,163,239 B2 | 4/2012 | Fujita |
| 8,178,043 B2 | 5/2012 | Burkhardt et al. |
| 8,187,558 B2 | 5/2012 | Jacobs et al. |
| 8,192,992 B2 | 6/2012 | Ammann et al. |
| 8,221,682 B2 | 6/2012 | Ammann et al. |
| 8,226,387 B2 | 6/2012 | Ignatiev |
| 8,234,941 B2 | 8/2012 | Fukuda et al. |
| 8,257,650 B2 | 9/2012 | Chow et al. |
| 8,257,664 B2 | 9/2012 | Ogusu |
| 8,262,994 B2 | 9/2012 | Hamada et al. |
| 8,262,999 B2 | 9/2012 | Kaneblei et al. |
| 8,266,973 B2 | 9/2012 | Maeda et al. |
| 8,293,191 B2 | 10/2012 | Kohara et al. |
| 8,309,358 B2 | 11/2012 | Ammann et al. |
| 8,318,500 B2 | 11/2012 | Ammann et al. |
| 8,329,101 B2 | 12/2012 | Fujita |
| 8,333,936 B2 | 12/2012 | Miyashita et al. |
| 8,337,753 B2 | 12/2012 | Ammann et al. |
| 8,343,423 B2 | 1/2013 | Mori et al. |
| 8,343,754 B2 | 1/2013 | Wittwer et al. |
| 8,343,770 B2 | 1/2013 | Hamada et al. |
| 8,354,078 B2 | 1/2013 | Shohmi et al. |
| 8,355,132 B2 | 1/2013 | Xia et al. |
| 8,356,525 B2 | 1/2013 | Hamada et al. |
| 8,357,538 B2 | 1/2013 | Self et al. |
| 8,366,997 B2 | 2/2013 | Degroot |
| 8,383,039 B2 | 2/2013 | Zhou et al. |
| 8,431,079 B2 | 4/2013 | Rosenberg et al. |
| 8,501,496 B2 | 8/2013 | Zuk et al. |
| 8,545,757 B2 | 10/2013 | Utsugi et al. |
| 8,556,564 B2 | 10/2013 | Miller |
| 2002/0155590 A1 | 10/2002 | Gebrian et al. |
| 2002/0164807 A1 | 11/2002 | Itaya et al. |
| 2004/0134750 A1 | 7/2004 | Luoma, II |
| 2005/0014285 A1 | 1/2005 | Miller |
| 2005/0220670 A1 | 10/2005 | Palmieri et al. |
| 2005/0249634 A1 | 11/2005 | Devlin, Sr. |
| 2006/0159587 A1 | 7/2006 | Fechtner et al. |
| 2006/0263248 A1 | 11/2006 | Gomm et al. |
| 2006/0286004 A1 | 12/2006 | Jacobs et al. |
| 2007/0010019 A1 | 1/2007 | Luoma, II |
| 2007/0059209 A1 | 3/2007 | Pang et al. |
| 2007/0092390 A1 | 4/2007 | Ignatiev et al. |
| 2008/0145939 A1 | 6/2008 | Jakubowicz et al. |
| 2009/0017491 A1 | 1/2009 | Lemme et al. |
| 2009/0148345 A1 | 6/2009 | Hamazumi et al. |
| 2009/0227033 A1 | 9/2009 | Hamada et al. |
| 2009/0258414 A1 | 10/2009 | Wittwer et al. |
| 2010/0111765 A1 | 5/2010 | Gomm et al. |
| 2010/0126286 A1 | 5/2010 | Self et al. |
| 2010/0187253 A1 | 7/2010 | Vincent et al. |
| 2010/0205139 A1 | 8/2010 | Xia et al. |
| 2010/0276445 A1 | 11/2010 | Jacobs et al. |
| 2010/0330609 A1 | 12/2010 | Nagai et al. |
| 2010/0332144 A1 | 12/2010 | Nagai et al. |
| 2011/0044834 A1 | 2/2011 | Ignatiev |
| 2011/0097240 A1 | 4/2011 | Yamashita et al. |
| 2011/0157580 A1 | 6/2011 | Nogami et al. |
| 2011/0293475 A1 | 12/2011 | Rosenberg et al. |
| 2011/0312082 A1 | 12/2011 | Silverbrook et al. |
| 2012/0039748 A1 | 2/2012 | Mimura et al. |
| 2012/0039771 A1 | 2/2012 | Utsugi et al. |
| 2012/0114526 A1 | 5/2012 | Watanabe et al. |
| 2012/0156764 A1 | 6/2012 | Kondo |
| 2012/0183438 A1 | 6/2012 | Shiba et al. |
| 2012/0218854 A1 | 8/2012 | Behringer et al. |
| 2012/0258004 A1 | 10/2012 | Ignatiev et al. |
| 2012/0294763 A1 | 11/2012 | Fukuda et al. |
| 2012/0301359 A1 | 11/2012 | Kraemer et al. |
| 2013/0017535 A1 | 1/2013 | Frey et al. |
| 2013/0064737 A1 | 3/2013 | Mori et al. |
| 2013/0065797 A1 | 3/2013 | Silbert et al. |
| 2013/0078617 A1 | 3/2013 | Ueda et al. |
| 2013/0089464 A1 | 4/2013 | Sakashita et al. |
| 2013/0112014 A1 | 5/2013 | Hamada et al. |
| 2013/0280129 A1 | 10/2013 | Watanabe et al. |
| 2013/0280130 A1 | 10/2013 | Sarwar et al. |
| 2013/0323758 A1 | 12/2013 | Oguri et al. |
| 2014/0011295 A1 | 1/2014 | Ammann et al. |
| 2014/0147922 A1 | 5/2014 | Knofe et al. |
| 2014/0248619 A1 | 9/2014 | Ammann et al. |
| 2015/0037211 A1 | 2/2015 | Wang et al. |

FOREIGN PATENT DOCUMENTS

| | | |
|---|---|---|
| EP | 0576291 | 12/1993 |
| EP | 0779514 | 6/1997 |
| EP | 0871892 | 6/1997 |
| EP | 0831330 | 3/1998 |
| EP | 1414573 | 3/2003 |
| EP | 2068154 | 6/2009 |
| EP | 2362228 | 8/2011 |
| EP | 2808683 | 12/2014 |
| JP | 357019667 | 2/1982 |
| JP | 359116047 | 7/1984 |
| JP | 61095248 | 5/1986 |
| JP | 05026883 | 2/1993 |
| JP | 406027004 | 2/1994 |
| JP | 407181129 | 7/1995 |
| JP | H1062432 | 3/1998 |
| JP | H10142232 | 5/1998 |
| JP | 03582240 | 10/2004 |
| JP | 2005128037 | 5/2005 |
| JP | 2005533641 | 10/2005 |
| JP | 2008224439 | 9/2008 |
| JP | 2008309661 | 12/2008 |
| JP | 2009031204 | 2/2009 |
| JP | 2009145202 | 7/2009 |
| JP | 2010217047 | 9/2010 |
| JP | 2011149832 | 8/2011 |
| JP | 2012021926 | 2/2012 |
| JP | 2012132721 | 7/2012 |
| JP | 2012173180 | 9/2012 |
| JP | 2012189611 | 10/2012 |
| JP | 2012233923 | 11/2012 |

(56) References Cited

FOREIGN PATENT DOCUMENTS

| JP | 2012251804 | 12/2012 |
|---|---|---|
| JP | 2012251909 | 12/2012 |
| JP | 2012255664 | 12/2012 |
| JP | 05178891 | 4/2013 |
| WO | 9315408 | 8/1993 |
| WO | 9722006 | 6/1997 |
| WO | 03018195 | 3/2003 |
| WO | 2010095375 | 8/2010 |
| WO | 2010106885 | 9/2010 |
| WO | 2010026837 | 11/2010 |
| WO | 2012114675 | 8/2012 |
| WO | 2012137019 | 10/2012 |
| WO | 2013111484 | 1/2013 |
| WO | 2013053023 | 4/2013 |
| WO | 2013064561 | 5/2013 |
| WO | 2013064562 | 5/2013 |

OTHER PUBLICATIONS

Invitation to Pay Additional Fees and, Where Applicable, Protest Fee and Communication Relating to the Results of the Partial International Search, issued by the International Searching Authority in connection with corresponding International patent application No. PCT/US2013/078041, dated Apr. 9, 2014, 6 pages.

International Preliminary Report on Patentability and Written Opinion, issued by the International Searching Authority in connection with International patent application No. PCT/US2013/078041, dated Sep. 24, 2015, 11 pages.

Communication Pursuant to Rules 161 and 162 EPC, issued by the European Patent Office in connection with European Patent Application 13824275.5 on Oct. 23, 2015, 2 pages.

International Search Report and Written Opinion, issued by the International Searching Authority in connection with corresponding International patent application No. PCT/US2014/029138, dated Jun. 23, 2014, 8 pages.

International Search Report and Written Opinion, issued by the International Searching Authority in connection with corresponding International patent application No. PCT/US2014/029118, dated Jun. 27, 2014, 9 pages.

Notification of the First Office Action and Search Report, issued by the State Intellectual Property Office of the P.R. China, in connection with Chinese Patent Application No. 201380076589.7, dated Jun. 21, 2016, 21 pages.

Japanese Patent Office, "Notice of Rejection," issued in connection with Japanese Patent Application No. 2016-500149, dated Oct. 4, 2016, 6 pages.

DIAGNOSTIC ANALYZERS WITH PRETREATMENT CAROUSELS AND RELATED METHODS

RELATED APPLICATION

This application claims the benefit under 35 U.S.C. § 119(e) to U.S. Provisional Application 61/792,779 titled "DIAGNOSTIC ANALYZERS WITH PRETREATMENT CAROUSELS AND RELATED METHODS," filed Mar. 15, 2013, which is incorporated herein by this reference in its entirety.

FIELD OF THE DISCLOSURE

The present disclosure relates generally to automated diagnostic analyzers and, more particularly, to automated diagnostic analyzers with pretreatment carousels and related methods.

BACKGROUND

Automated diagnostic analyzers employ multiple carousels and multiple pipetting mechanisms to automatically aspirate fluid from and dispense fluid to different areas in the analyzer to perform diagnostic analysis procedures. Some known analyzers include a reaction vessel carousel having multiple reaction vessels and modules around the carousel to perform various functions on the reaction vessels as the carousel rotates. The diagnostic analyzers perform different diagnostic tests depending on the type of sample and/or the type of testing desired. Different diagnostic tests may involve different amounts of time for incubation, mixing, reading and other assay steps. Known analyzers that accommodate testing procedures that include relatively long and/or otherwise detailed steps that increase the duration of a test have low throughput.

DETAILED DESCRIPTION

Figure 1:
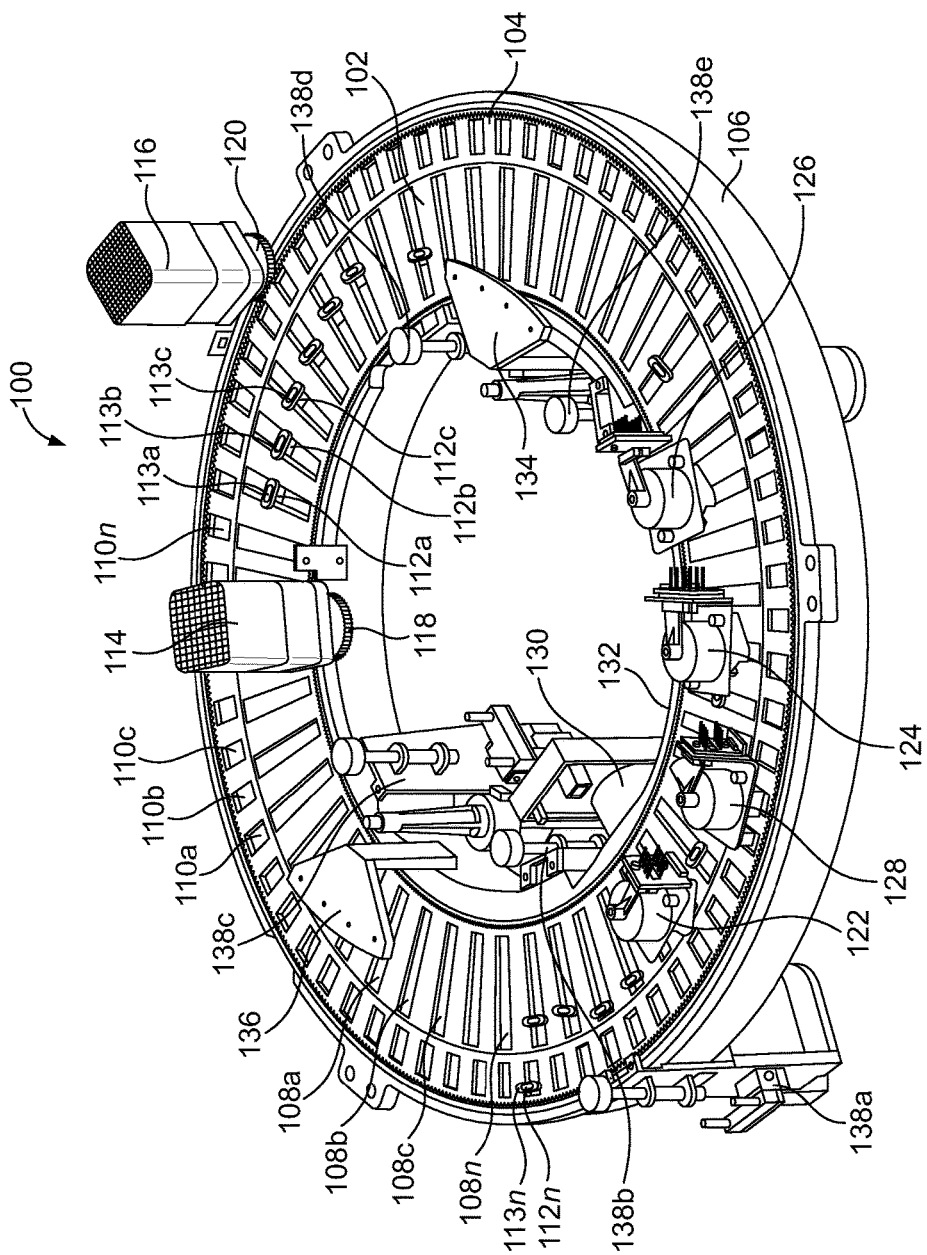
FIG. 1 illustrates a perspective view of an example processing track having concentric carousels in accordance with the teachings of this disclosure.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

Diagnostics laboratories employ diagnostic instruments such as those for testing and analyzing specimens or samples including, for example, clinical chemistry analyzers, immunoassay analyzers and hematology analyzers. Specimens and biological samples are analyzed to, for example, check for the presence or absence of an item of interest including, for example, a specific region of DNA, mitochondrial DNA, a specific region of RNA, messenger RNA, transfer RNA, mitochondrial RNA, a fragment, a complement, a peptide, a polypeptide, an enzyme, a prion, a protein, an antibody, an antigen, an allergen, a part of a biological entity such as a cell or a viron, a surface protein, and/or functional equivalent(s) of the above. Specimens such as a patient's body fluids (e.g., serum, whole blood, urine, swabs, plasma, cerebra-spinal fluid, lymph fluids, tissue solids) can be analyzed using a number of different tests to provide information about the patient's health.

Generally, analysis of a test sample involves the reaction of test samples with one or more reagents with respect to one or more analytes. The reaction mixtures are analyzed by an apparatus for one or more characteristics such as, for example, the presence and/or concentration of a certain analyte in the test sample. Use of automated diagnostic analyzers improves the efficiency of the laboratory procedures because the technician (e.g., an operator) has fewer tasks to perform and, thus, the potential for operator or technician error is reduced. In addition, automated diagnostic analyzers also provide results much more rapidly and with increased accuracy and repeatability.

Automated diagnostic analyzers use multiple pipettes to move liquids between storage containers (e.g., receptacles such as open topped tubes) and containers in which the specimens are to be processed (e.g., reaction vessels). For example, a specimen may be contained in a tube loaded in a rack on an analyzer, and a head carrying a pipette moves the pipette into the tube where a vacuum is applied to extract a selected amount of the specimen from the tube into the pipette. The head retracts the pipette from the tube and moves to another tube or reaction vessel located at a processing station and deposits the extracted specimen from the pipette into the reaction vessel. A reagent is similarly acquired from a reagent supply.

Some diagnostic analyzers employ a processing carousel having a plurality of reaction vessels to conduct diagnostic tests. As the processing carousel rotates, multiple functions and diagnostic testing procedures are performed on the individual reaction vessels. Some diagnostic tests require a longer incubation time for effective reaction between the sample and the one or more reagents than other tests. Some known analyzers include a single processing track and conduct different testing procedures including those that involve longer reacting tests in the single processing track of the analyzer. Thus, the assay steps and scheduling protocols are developed based on the test durations, and the longest type of test determines the throughput of the analyzer. In addition, some tests, such as for example, those with relatively faster reactions and/or lower incubation periods, remain idle for periods of time.

The example analyzers and/or processing tracks disclosed herein include a pretreatment carousel for the performance of testing procedures that occur in preparation for a diagnostic test such as, for example, incubation, dilution, etc. In some examples, the pretreatment carousel is positioned coplanar and concentric with a main processing carousel. Pretreatment operations are performed in a plurality of reaction vessels on the pretreatment carousel and then the contents or portions of the contents of the reaction vessels are transferred to other reaction vessels on the main processing carousel for analysis. Therefore, the pretreatment operations occur in a different area outside of the main processing carousel and, thus, diagnostic testing timing and throughput may be increased on the main processing carousel.

The example analyzers and/or processing tracks disclosed herein also include multiple pipetting mechanisms positioned around the processing track to aspirate and/or dispense liquids to and from different locations on the carousels. In some examples, a first pipetting mechanism is used to dispense a sample into a reaction vessel on the main processing carousel and may also be used to transfer a pretreated sample from the pretreatment carousel to the main processing carousel. In some examples, one or more other pipetting mechanism(s) may be used to dispense one or more reagent(s) into one or more reaction vessel(s) during a test such as, for example, at different times during diagnostic testing and/or at different locations on the carousels.

In some examples, the analyzers and/or processing tracks disclosed herein are used for immunoassays, which are biochemical tests that measure the concentration of a substance in a biological liquid, e.g., serum, using the reaction of an antibody and respective antigen. A particular type of immunoassay known as chemiluminescent microparticle immunoassay and/or a chemiluminescent magnetic immunoassay involves magnetic or paramagnetic materials and a chemiluminescent label conjugated to an antibody or an antigen. In this assay, a magnetic microparticle is coated with a first antibody. A second antibody is labeled with a chemiluminescent label and not attached to a magnetic microparticle. The antibodies and corresponding antigens react and the attached chemiluminescent label produces measurable light indicative of the amount of analyte present in the sample.

In other examples, the example analyzers and/or processing tracks disclosed herein are used for clinical chemistry assays, which are biochemical tests that measure the concentration of a substance from, for example, blood or urine. The concentrations indicate the condition or state of health of the various systems of the body.

An example apparatus disclosed herein includes a first carousel comprising a first annular array of slots to receive a first vessel, a first track of rotation about the first carousel having a first diameter and a second track of rotation about the first carousel having a second diameter smaller than the first diameter. The example apparatus includes a first diverter to move the first vessel from the first track to the second track. The example apparatus also includes a second carousel coaxial with the first carousel, the second carousel comprising a second annular array of slots to receive a second vessel. In some examples, the second carousel is concentric to the first carousel.

In some examples, the apparatus also includes a second diverter to move the first vessel from one portion of the second track to another portion of the second track. In some examples, apparatus also includes a third diverter to move the first vessel from the second track to a wash station. In some such examples, the apparatus also includes a fourth diverter to remove the second vessel from the second carousel.

In some examples, the first carousel includes a first inner circumference and a first outer circumference, the second carousel includes a second inner circumference and a second outer circumference, and the second inner circumference is disposed outside of the first outer circumference. In some such examples, the apparatus includes a first pipetting mechanism disposed outside of the second outer circumference. The example first pipetting mechanism is to aspirate from a first container disposed outside of the second outer circumference and to dispense to at least one of the first vessel on the first carousel or the second vessel on the second carousel. In some examples, the first pipetting mechanism is to aspirate from the second vessel on the second carousel and to dispense to the first vessel on the first carousel.

In some examples, the apparatus includes a second pipetting mechanism disposed outside of the second outer circumference. The example second pipetting mechanism is positioned to aspirate from a second container disposed outside of the second outer circumference. The second pipetting mechanism also is to aspirate from and/or dispense to the second vessel on the second carousel and to dispense to the first vessel on the first carousel.

In some such examples, the first pipetting mechanism has a first pipette arm that is movable along a first path of travel over the first vessel on the first carousel and the second vessel on the second carousel, and the second pipetting mechanism has a second pipette arm that is movable along a second path of travel over a third vessel on the first carousel and a fourth vessel on the second carousel. In some examples, the first path of travel intersects the first carousel in two locations and the second carousel in two locations.

In some examples, the apparatus also includes a third pipetting mechanism disposed inside of the first inner circumference. The example third pipetting mechanism is positioned to aspirate from a third container disposed inside of the first inner circumference and to dispense into the first vessel on the first carousel. In some such examples, the third pipetting mechanism is offset from a first axis about which the first carousel and the second carousel are to rotate. In some examples, at least one of the second container or the third container is disposed below the first carousel.

In some examples, the first pipetting mechanism is to dispense to the first vessel when the first vessel is on the first track of the first carousel. In some such examples, the second pipetting mechanism is to dispense to the first vessel when the first vessel is on the first track of the first carousel. In some examples, the third pipetting mechanism to dispense to the first vessel when the first vessel is on the second track of the first carousel. In some examples, the second pipetting mechanism is to dispense a paramagnetic microparticle liquid into at least one of the first vessel on the first carousel or the second vessel on the second carousel.

In some examples, each of the slots is elongated to receive more than one vessel. In some examples, a first slot of the first annular array of slots is to receive the first vessel in the first track and a third vessel in the second track. In some examples, the second annular array of slots comprises a greater number of slots than the first annular array of slots.

In some examples, the second track comprises a spiral track, wherein the first vessel in one of the first annular array of slots on the first carousel follows the spiral track as the first carousel rotates. In some such examples, the spiral track decreases in diameter to lead the first vessel from an outer radial position on the first carousel to an inner radial position on the first carousel. In some examples, the first vessel in one of the first annular array of slots is to move from the outer radial position to the inner radial position after at least two rotations of the first carousel.

In some examples, the first carousel rotates in a plurality of intervals, each interval comprising an advancement and a stop. In some such examples, each interval of the first carousel is about 18 seconds. In some examples, the second carousel rotates in a plurality of intervals, each interval comprises a major interval and a minor interval. In some examples, the minor interval of the second carousel comprises an advancement and a stop, and the major interval of the second carousel comprises an advancement and a stop. In some such examples, each interval of the second carousel is about 18 seconds. In some examples, the major interval is about 16 seconds.

Another example apparatus disclosed herein includes a first carousel rotatably coupled to a base. The example first carousel has a first diameter and a first annular array of slots to receive a first plurality of vessels. The example apparatus also includes a second carousel rotatably coupled to the base. The example second carousel is coaxial with the first carousel, has a second diameter larger than the first diameter and has second annular array of slots to receive a second plurality of vessels. The example apparatus includes a first pipetting mechanism disposed outside of the first diameter and outside of the second diameter. The example first pipetting mechanism is positioned to aspirate from a first container disposed outside of the first diameter and the second diameter and to dispense to one of the first plurality of vessels on the first carousel and one of the second plurality of vessels on the second carousel. The example apparatus also includes a second pipetting mechanism disposed outside of the first diameter and outside of the second diameter. The second pipetting mechanism of the example apparatus is positioned to aspirate from a second container disposed outside of the first diameter and the second diameter, to aspirate from or dispense to one of the second plurality of vessels on the second carousel, and to dispense to one of the plurality of vessels on the first carousel.

The example apparatus also includes a third pipetting mechanism disposed within the first diameter and within the second diameter, and the third pipetting mechanism is positioned to aspirate from a third container disposed within the first diameter and the second diameter and to dispense to one of the first plurality of vessels on the first carousel. In some examples, the third pipetting mechanism is offset from an axis of rotation of the first carousel.

In some examples, the second carousel is concentric with the first carousel. In some examples, the first pipetting mechanism has a first pipette arm that is movable along a first path of travel over a first vessel of the first plurality of vessels on the first carousel and a second vessel of the second plurality of vessels on the second carousel. In some such examples, the second pipetting mechanism has a second pipette arm that is movable along a second path of travel over a third vessel of the first plurality of vessels on the first carousel and a fourth vessel of the second plurality of vessels on the second carousel. In some examples, the third pipetting mechanism has a third pipette arm that is movable along a third path of travel over a fifth vessel of the first plurality of vessels on the first carousel. In some examples, at least one of the first pipetting mechanism, the second pipetting mechanism or the third pipetting mechanism is movable in a substantially vertical direction.

In some examples, the first carousel comprises a spiral track, and a first vessel of the first plurality of vessels in one of the first annular array of slots on the first carousel follows the spiral track as the first carousel rotates. In some such examples, the spiral track is to lead the first vessel from an outer radial location on the first carousel to an inner radial location on the first carousel. In some examples, the first carousel comprises a plurality of diverters to divert one or more of the first plurality of vessels from one location on the spiral track to another location on the spiral track.

An example method disclosed herein comprises rotating a first carousel relative to a base. In the example method, the first carousel comprises a first annular array of slots to receive a first plurality of vessels, a first track of rotation about the first carousel having a first diameter and a second track of rotation about the first carousel having a second diameter smaller than the first diameter. The example method includes diverting at least one of the first plurality of vessels from the first track to the second track. The example method also includes rotating a second carousel relative to the base, the second carousel being coaxial with the first carousel, the second carousel comprising a second annular array of slots to receive a second plurality of vessels.

In some examples, the second carousel is concentric with the first carousel. In some examples, the method includes diverting at least one of the first plurality of vessels from one location on the second track to another location on the second track. In some such examples, the method includes diverting at least one of the first plurality of vessels from the second track to a wash station.

In some examples, the first carousel comprises a first diameter and the second carousel comprises a second diameter larger than the first diameter. In some examples, the method includes aspirating a first fluid from a first container disposed outside of the first diameter and the second diameter and dispensing the first fluid into at least one of the first plurality of vessels on the first carousel or one of the second plurality of vessels on the second carousel. In some such examples, the method includes aspirating a second fluid from one of the second plurality of vessels on the second carousel and dispensing the second fluid into one of the first plurality of vessels on the first carousel.

In some examples, the method includes aspirating a third fluid from a second container disposed outside of the first diameter and the second diameter and dispensing the third fluid into at least one of the first plurality of vessels on the first carousel or one of the second plurality of vessels on the second carousel. In some such examples, the method includes the method includes aspirating the third fluid from the second container, aspirating a fourth fluid from one of the second plurality of vessels on the second carousel and dispensing the third fluid and the fourth fluid into one of the first plurality of vessels on the first carousel. In some examples, the method includes aspirating a fifth fluid from a third container disposed within the first diameter and the second diameter and dispensing the fifth fluid into one of the first plurality of vessels on the first carousel. In some such examples, the fifth fluid is dispensed into one of the first plurality of vessels when the vessel is on the second track of rotation.

In some examples, the method includes rotating the first carousel to transport one of the vessels of the first plurality of vessels on the second track of rotation from an outer radial location on the first carousel to an inner radial location on the first carousel. In some such examples, the second track of rotation comprises a spiral, and rotating one of the first plurality of vessels on the second track moves the vessel from the outer radial location to the inner radial location. In some examples, the first carousel is to complete at least two rotations to transport the vessel from the outer radial location to the inner radial location on the first carousel.

Another example method is disclosed here that includes rotating a first carousel relative to a base. The example first carousel has a first diameter and a first annular array of slots to receive a first plurality of vessels. The example method also includes rotating a second carousel relative to the base. The example second carousel is coaxial with the first carousel, and the example second carousel has a second diameter larger than the first diameter and a second annular array of slots to receive a second plurality of vessels.

The example method includes aspirating a first fluid (e.g., a sample) from a first container outside of the first diameter and the second diameter via a first pipetting mechanism. The example first pipetting mechanism is positioned outside of the first diameter and outside of the second diameter. The example method includes dispensing the first fluid, via the first pipetting mechanism, into at least one of one of the first plurality of vessels on the first carousel or one of the second plurality of vessels on the second carousel. The example method also includes aspirating a second fluid from a second container outside of the first diameter and the second diameter via a second pipetting mechanism. The example second pipetting mechanism is positioned outside of the first diameter and outside of the second diameter. The example method includes dispensing the second fluid, via the second pipetting mechanism, into at least one of one of the first plurality of vessels on the first carousel or one of the second plurality of vessels on the second carousel. The example method includes aspirating a third fluid from a third container disposed within the first diameter and the second diameter via a third pipetting mechanism. The example third pipetting mechanism is positioned inside of the first diameter and the second diameter. The example method also includes dispensing the third fluid, via the third pipetting mechanism, into one of the first plurality of vessels on the first carousel.

In some examples, the second carousel is concentric with the first carousel. In some examples, the method includes aspirating, via the first pipetting mechanism, a fourth fluid from one of the second plurality of vessels on the second carousel and dispensing, via the first pipetting mechanism, the fourth fluid into one of the first plurality of vessels on the first carousel. In some such examples, the method includes aspirating, via the second pipetting mechanism, a fifth fluid from one of the second plurality of vessels on the second carousel and dispensing, via the second pipetting mechanism, the fifth fluid into one of the first plurality of vessels on the first carousel.

In some examples, the first carousel comprises a first track of rotation and a second track of rotation. The example second track of rotation comprises a spiral track. In some such examples, the method includes rotating the first carousel to transport one of the first plurality of vessels along the second track. In some examples, rotating the one of the first plurality of vessels along the second track moves the vessel from an outer radial location on the first carousel to an inner radial location on the first carousel.

In some examples, the method includes diverting, via a first diverter, one of the first plurality of vessels from the first track to the second track. In some such examples, the method includes diverting, via a second diverter, one of the first plurality of vessels from a first location on the second track to a second location on the second track. In some examples, the method includes diverting, via a third diverter, one of the first plurality of vessels from the second track of rotation to a wash station.

In some examples, the method includes rotating the first carousel in a plurality of intervals, each interval having and advancement and a stop. In some examples, each of the intervals of the first carousel is about 18 seconds. In some examples, the method includes rotating the second carousel in a plurality of minor intervals and major intervals. In some examples, the minor interval has an advancement and a stop, and the major interval has an advancement and a stop. In some examples, each of the minor intervals of the second carousel is about two seconds. In some such examples, each of the major intervals of the second carousel is about 16 seconds.

In another example disclosed herein, an example apparatus includes a carousel having an outer edge, an inner edge and annular array of elongated slots extended between the out edge and the inner edge to receive a plurality of vessels. In addition, the example carousel includes a spiral track extending from the outer edge to the inner edge in a spiral rotation (e.g., coiled, corkscrewed, helical, etc.) to guide a vessel from a first position adjacent the outer edge to a second position adjacent the inner edge.

In some examples, the example apparatus includes a diverter to move the vessel from a first location on the spiral track to a second location on the spiral track. In some examples, the example apparatus includes a circular track surrounding the spiral track. Also, in some examples, the example apparatus includes a diverter to move a vessel from the circular track to the spiral track.

Also disclosed herein is an example apparatus that includes a carousel having an annular array of slots to receive a plurality of vessels. The example apparatus also includes a first track of rotation about the carousel having a first circumference and a second track of rotation about the carousel disposed within the first circumference, the second track comprising a spiral path.

In some examples, the example apparatus includes a diverter to move a vessel from the first track to the second track. In some examples, the example apparatus includes a diverter to move one of the plurality of vessels from one portion of the second track to another portion of the second track. In some examples, the example apparatus includes a diverter to move one of the plurality of vessels from the second track to a side track. Also, in some examples, the side track leads to a wash station.

In some examples, each of the slots of the example apparatus is elongated to receive more than one vessel. In some examples, when a first vessel is in one of the annular array of slots and is engaged with the second track. The first vessel follows the spiral path as the carousel rotates. In some examples, the first vessel is to move from an outer radial position on the carousel an inner radial position on the carousel as the carousel rotates.

In some examples, the first track is disposed above the carousel and a vessel on the carousel is to engage the first track when the vessel is disposed in one of the annular array of slots. Also in some examples, the second track is disposed above the carousel and a vessel on the carousel is to engage the second track when the vessel is disposed in one of the annular array of slots. In some examples, a first vessel and a second vessel are disposed in the same slot. In addition, in some examples, the example apparatus also includes a cover to cover the carousel, wherein the first track and the second track are coupled to a bottom surface of the cover.

In some examples, the example apparatus includes a heat block disposed below the carousel. The heat block, in some examples, includes a plurality grooves substantially aligned with the first track and the second track. In addition, in some examples, when a vessel is disposed in one of the annular array of slots on the first carousel, at least a portion of the vessel is disposed within one of the plurality of grooves in the heat block.

Also disclose herein is an example method that includes rotating a first carousel having a first vessel through a first plurality of intervals, each of the first plurality of intervals comprising a first advancement and a first stop. The example method also includes rotating a second carousel having a second vessel through a second plurality of intervals, each of the second plurality of intervals comprising a second advancement, a second stop, a third advancement and a third stop.

In some examples, the duration of the first plurality of intervals is substantially the same the duration of the second plurality of intervals. Also, in some examples, the second stop is shorter than the third stop.

Also disclosed herein is an example apparatus that includes a first carousel having a first inner circumference and a first outer circumference. The example apparatus also includes a second carousel having a second inner circumference and a second outer circumference. In this example, the second inner circumference is disposed outside of the first outer circumference. The example apparatus also includes a first pipetting mechanism to rotate along a first path of travel to access the first carousel in a first position and the second carousel in a second position.

In some examples, the first carousel and the second carousel are independently rotatable. In some examples, the example apparatus includes a first motor to rotate the first carousel and a second motor to rotate the second carousel. In some examples, the first carousel is to rotate in first locksteps, and the second carousel is rotate in a second locksteps. Also, in some examples, a first duration of the first locksteps is different than a second duration of the second locksteps.

In some examples, the first pipetting mechanism is to access a sample disposed outside of the second outer circumference. Also, in some examples, the first pipetting mechanism is disposed outside of the second outer circumference.

In some examples, the example apparatus includes a second pipetting mechanism that is to rotate along a second path of travel to access the first carousel in a third position and the second carousel in a fourth position. In some example, the second pipetting mechanism is disposed out-side of the second outer circumference. Also, in some examples, the second pipetting mechanism is to access a third carousel. In addition, in some examples, the third carousel is distanced vertically from the first carousel.

In some examples, the example apparatus includes a second pipetting mechanism that is to rotate along a second path of travel to access the first carousel in a third position and a third carousel in a fourth position. In some examples, the second pipetting mechanism is disposed inside of the first inner circumference. Also, in such examples, the third carousel may be is distanced vertically (e.g., above or below) the first carousel.

Turning now to the figures, an example processing track 100 is shown in FIG. 1 as having a first carousel 102 (e.g., an annular plate, a track, a disc, a revolving belt, etc.) and a second carousel 104 and a housing 106. The example processing track 100 may be used, for example, to conduct immunoassays, clinical chemistry assays and/or other types of diagnostic tests. The example processing track 100 may be incorporated in an analyzer having automated reagent and/or sample access such, as for example, the analyzer 200 (FIG. 2) disclosed in detail below. In some examples, the first carousel 102 is the main processing carousel for conducting diagnostic tests, and the second carousel 104 is a pretreatment path or track for preparing and treating liquids (e.g., samples) to be used in the diagnostic tests on the first carousel 102. In some examples, the second carousel 104 enables one or more reactions to incubate or react prior to performing the diagnostic testing and analyzing the sample in the main processing path of the first carousel 102. However, in other examples, these carousels may be switched and the first carousel 102 may be used for treating liquids for diagnostic testing on the second carousel 104.

In the example shown in FIG. 1, the first and second carousels 102, 104 are rotatable within the housing 106, and the first and second carousels 102, 104 are concentric and coplanar with each other within the housing 106. In the example shown, the first carousel 102 includes a first plurality of slots 108a-n and the second carousel 104 includes a second plurality of slots 110a-n. The slots 108a-n, 110a-n of the respective first and second carousels 102, 104 are arranged in an annular orientation around the respective first and second carousels 102, 104. In the example shown, the first carousel 102 has 46 slots 108a-n, and the second carousel 104 has 61 slots 110a-n. However, in other examples, the first and second carousels 102, 104 may have more or fewer slots.

The first plurality of slots 108a-n and the second plurality of slots 110a-n are to hold vessels 112a-n, which may be, for example reaction vessels. In the example shown, the vessels 112a-n are disposable cuvettes (e.g., plastic cuvettes) that are discarded after one or more tests. However, in other examples, the vessels 112a-n are reusable cuvettes (e.g., washable glass cuvettes). In such examples, after a test has been completed in one of the vessels 112a-n, the vessel 112a-n is cleaned (e.g., sterilized), and the vessel 112a-n may be used for another test. As shown in FIG. 1, one or more vessels 112a-n may be placed in the first plurality of slots 108a-n and/or the second plurality of slots 110a-n and rotated around the processing track 100. In the example shown, the first plurality of slots 108a-n are elongated such that each of the slots 108a-n may retain more than one reaction vessel 112a-n (e.g., two or three reaction vessels 112a-n).

In some examples, the example reaction vessels 112a-n include rims 113a-n (e.g., flanges, ears) (shown in FIG. 4B) that extend outward from the top of the vessel body and are used to support the reaction vessels 112a-n on the first and second carousels 102, 104 such that the bodies of the vessels extend through the slots 108a-n, 110a-n and hang downward beneath the first and second carousels 102, 104. In some examples, the rims 113a-n are unitary (e.g., a single mold) with the reaction vessels 112a-n. In other examples, the rims 113a-n may be separate components coupled to the reaction vessels 112a-n.

In the example shown in FIG. 1, a first motor 114 (e.g., an electric motor, a stepper motor, a servo motor, etc.) drives the first carousel 102 and a second motor 116 drives the second carousel 104. In the example shown, the first motor 114 has a first gear 118 to engage a plurality of teeth on the inside of the first carousel 102, and the second motor 116 has a second gear 120 to engage a plurality of teeth on the outside of the second carousel 104. The first and second motors 114, 116 operate to rotate the first and second carousels 102, 104, respectively, independent of each other, in either direction and according to a programming and scheduling protocol of the analyzer. In other examples, other types of motors and/or drive mechanisms may be used to rotate to the first and second carousels 102, 104. In some examples, the first and second motors 114, 116 are coupled (e.g., mounted) to the housing 106 and positioned to engage the respective carousels 102, 104. In other examples, the first and second motors 114, 116 may be coupled to a lid (e.g., a cover 424 shown in FIGS. 4D and 4E) on the processing track 100 or other surfaces of the analyzer upon which the processing track 100 is installed.

In the example shown in FIG. 1, the processing track 100 includes a first diverter 122, a second diverter 124, a third diverter 126 and a fourth diverter 128. The first, second and third diverters 122-126 operate to move vessels 112a-n on the first carousel 102 to different positions along a track system that is disposed within the housing 106 and beneath the first carousel 102, disclosed in detail below. The fourth diverter 128 (e.g., an active unloader) unloads vessels 112a-n from the second carousel 104, also described in further detail below. In the example shown, the diverters 122-128 are depicted on top of the carousels 102, 104. However, the diverters 122-128 are coupled to a stationary surface (e.g., a lid on the processing track 100 of the analyzer) above the carousels 102, 104 are not rotatable on the carousels 102, 104 themselves.

In the example shown, the processing track 100 also includes a reader 130 (e.g., an analyzer) disposed adjacent the first and second carousels 102, 104. In the illustrated example, the reader 130 is coupled to an inside bore 132 of the housing 106. The reader 130 analyzes the reactions within the vessels 112a-n as the vessels 112a-n pass in front of the reader 130. The processing track 100 also includes a first wash station 134 and a second wash station 136 coupled to the bore 132 of the housing 106. The first and second wash stations 134, 136 may be used, for example, to conduct magnetic microparticle processing, described in further detail below. In the example shown, a plurality of mixers or in-track vortexers (ITV) 138a-f are disposed around the processing track 100 to mix the contents of the vessels 112a-n at different locations and times during processing.

Figure 2:
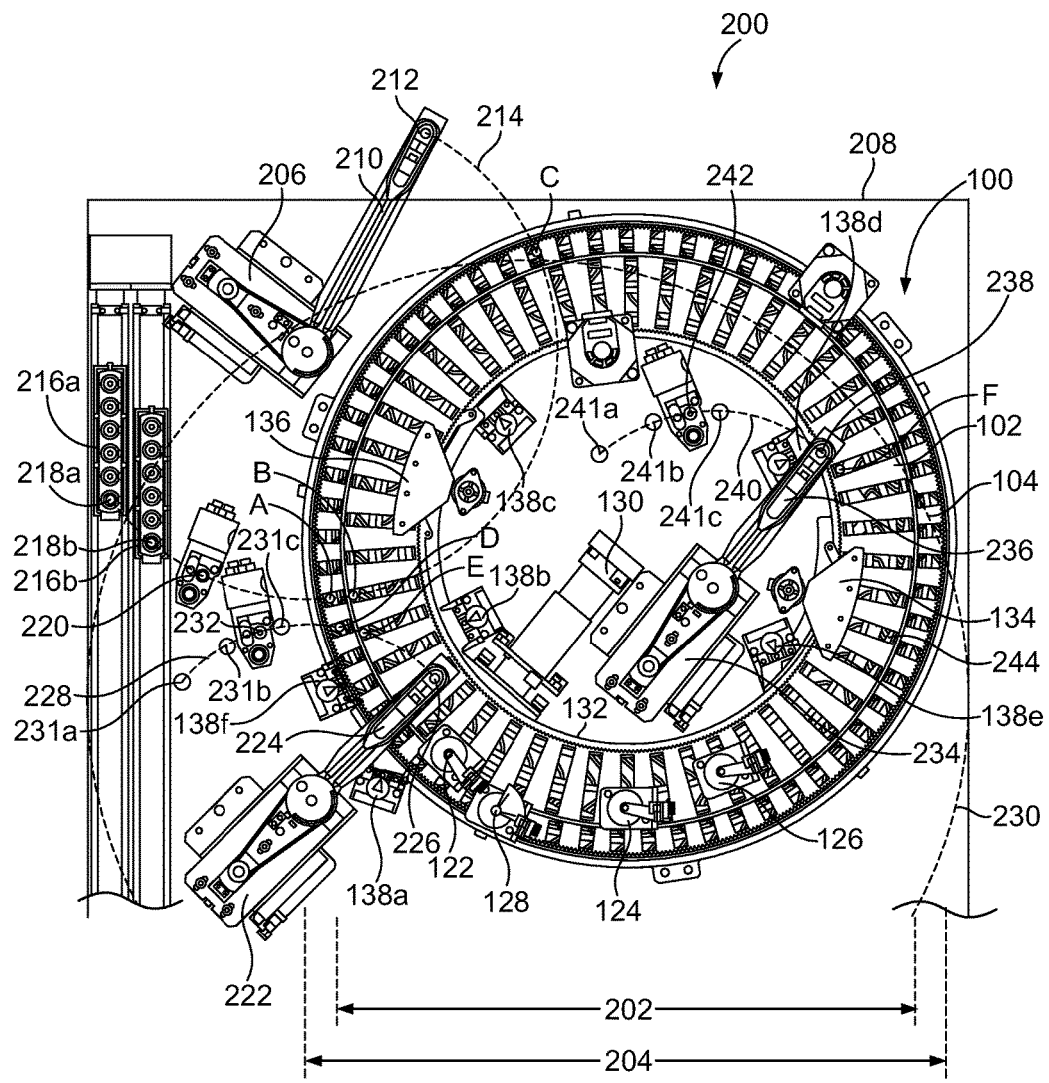
FIG. 2 shows a top plan view of an example diagnostic analyzer including the example processing track of FIG. 1.
Figure 3:
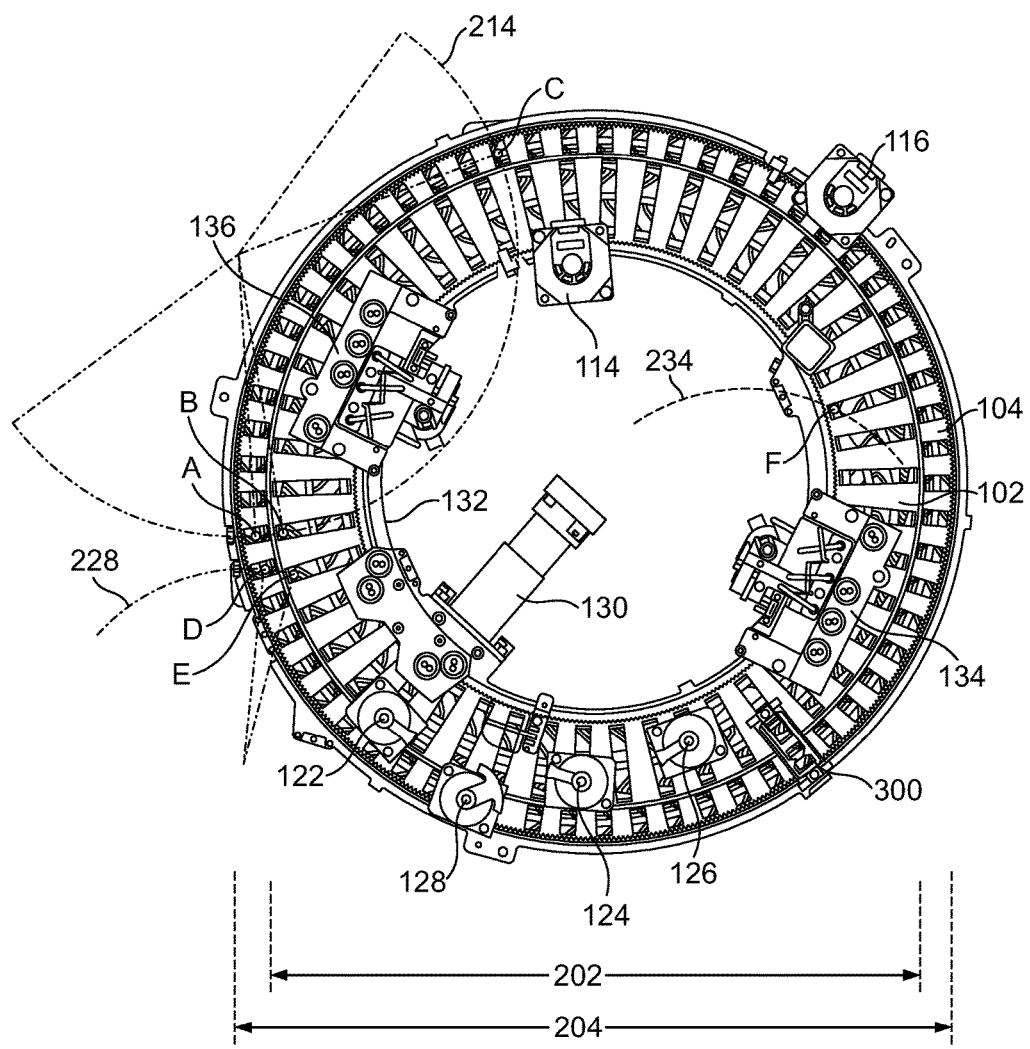
FIG. 3 shows a top plan view of the example processing track of FIG. 1.

FIG. 2 illustrates a top plan view of the example processing track 100 incorporated into an analyzer 200 including a plurality of pipetting mechanisms and other analysis components. FIG. 3 also illustrates a top plan view of the example processing track 100, but with the pipetting mechanisms and other analysis components removed for clarity. In the examples shown in FIGS. 2 and 3, the first carousel 102 has a first diameter 202 and the second carousel 104 has a second diameter 204. As shown, the second diameter 204 is greater than the first diameter 202, and the second carousel 104 is concentric (e.g., having the same center axis or coaxial) with and coplanar to the first carousel 102.

In the illustrated example shown in FIG. 2, the analyzer 200 includes a first pipetting mechanism 206. In some examples, the first pipetting mechanism 206 is coupled (e.g., mounted, fastened) to a base 208 of the analyzer 200. In the example shown, the first pipetting mechanism 206 is disposed outside of the first diameter 202 and outside of the second diameter 204 (e.g., at a distance from the center of the first carousel 102 and the center of the second carousel 104 that is greater than each of the radii of the first carousel 102 and the second carousel 104). The first pipetting mechanism 206 has multiple degrees of freedom. In the example shown, the first pipetting mechanism 206 has a first probe arm 210 that moves a first pipette 212 along a first path of travel 214 (e.g., a first horizontal arc, a first range of access) to aspirate/dispense liquid from containers or vessels along the first path of travel 214. The first path of travel 214 may be circular, semicircular, linear or a combination thereof. The first pipetting mechanism 206 is also movable in the Z direction (e.g., the vertical direction).

In the example shown, the first pipetting mechanism 206 may be used, for example, to dispense a sample (e.g., a test sample or a specimen) into one or more of the vessels 112a-n on the first carousel 102 and/or the second carousel 104. In some examples, a sample is aspirated from sample containers 216a-n (which may be in carriers 218a, 218b) along the first path of travel 214 of the first pipetting mechanism 206. The first probe arm 210 moves (e.g., rotates or pivots) along the first path of travel 214 to align the first pipette 212 of the first pipetting mechanism 206 above the sample tubes 216a-n. The first pipetting mechanism 206 moves the first pipette 212 downward into one of the sample containers 216a-n and aspirates an amount of sample.

In the example shown in FIGS. 2 and 3, the first pipetting mechanism 206 has access to vessels disposed within the slots 108a-n, 110a-n of the first and second carousels 102, 104 along the first path of travel 214. Specifically, the first pipetting mechanism 206 can access a vessel on the second carousel 104 at point A (e.g., a pretreat sample start position), a vessel on the first carousel 102 at point B, and another vessel on the second carousel 104 at point C. In the example shown, the first pipetting mechanism 206 is capable of aspirating from and/or dispensing to any location along the first path of travel 214. In the example shown, a wash zone 220 is also disposed along the first path of travel 214. The first pipetting mechanism 206 may access the wash zone 220 to clean the first pipette 212 such as, for example, between aspirations of different samples.

In some examples, the first pipetting mechanism 206 aspirates a sample (e.g., from sample container 216a or 216b) and dispenses the sample into a vessel on the second carousel 104 at point A for pretreatment and also dispenses sample into another vessel on the first carousel 102 at point B for processing on the first carousel 102 (e.g., the main processing path or track). In some examples, a sample is dispensed into a vessel on the second carousel 104 at point A and the second carousel 104 rotates in a counterclockwise direction to allow the sample and one or more reagents (disclosed in detail below) to react (e.g., incubate). The first pipetting mechanism 206 may then aspirate the pretreated sample from the vessel on the second carousel 104 at point C, after the sample has been pretreated (e.g., incubated). The first pipetting mechanism 206 may then dispense the pretreated sample into a vessel on the first carousel 102 at point B for processing on the first carousel 102.

In the example shown, the analyzer 200 includes a second pipetting mechanism 222. The second pipetting mechanism 222 may be coupled to, for example, the base 208 of the analyzer 200. The second pipetting mechanism 222 has multiple degrees of freedom. In the example shown, the second pipetting mechanism 222 has a second probe arm 224 that moves a second pipette 226 along a second path of travel 228 (e.g., a second horizontal arc, a second range of access) to aspirate/dispense liquid from locations along the second path of travel 228. The second path of travel 228 may be circular, semicircular, linear or a combination thereof. The second pipetting mechanism 222 is also movable in the Z direction (e.g., the vertical direction).

In the example shown in FIG. 2, the second pipetting mechanism 222 is used to aspirate a liquid (e.g., a reagent, a first reagent, a liquid containing magnetic particles) and dispense the liquid into one or more vessels on the first and second carousels 102, 104. In some examples, the second pipetting mechanism 222 is a first reagent pipette and is utilized to add a first reagent (e.g., a reagent containing magnetic microparticles) to vessels on the first and second carousels 102, 104. In some examples, reagent containers are disposed on a third carousel 230 (shown in shadow lines) partially disposed within the second path of travel 228. In some examples, the third carousel 230, having a plurality of reagent containers, is located below the processing track 100 (as shown in FIG. 2). In some examples, reagent containers are brought to a position along the second path of travel 228 such that the second pipetting mechanism 222 can move the second pipette 226 to a location above a reagent container and aspirate reagent from the container. For example, the second pipetting mechanism 222 may access a reagent container on the third carousel 230 at any of the access ports 231*a*, 231*b*, 231*c* located on the second path of travel 228. In some examples, the third carousel 230 includes a plurality of carriers each having one or more containers (e.g., reagent containers). In some examples, when the carriers are arranged on the third carousel 230, multiple annular arrays of containers are formed (e.g., an inner annular array of containers, a middle annular array of containers, an outer annular array of containers, etc.). In some examples, one or more containers in the outer annular array of containers include reagents (e.g., including microparticles) for diagnostic testing on the main processing track (e.g., the first carousel 102). In other examples, one or more containers in the outer annular array of containers hold reagents for use with pretreatment processing (e.g., on the second carousel 104).

After aspirating a liquid (e.g., a reagent), the second pipetting mechanism 222 rotates to dispense the liquid into vessels on the second carousel 104 at point D (e.g., a pretreat reagent start position) and/or other vessels on the first carousel 102 at point E. In some examples, the second pipetting mechanism 222 dispenses reagent into a vessel on the first or second carousel 102, 104 that has previously been loaded with a sample. In some examples, the sample and the reagent react as the second carousel 104 rotates and, in some examples, the mixture or a portion of the mixture is aspirated (e.g., via the first pipetting mechanism 206 at point C) from the vessel on the second carousel 104 and dispensed into another vessel on the first carousel 102 for processing.

In some examples, the second pipetting mechanism 222 aspirates the contents of a vessel on the second carousel 104 at point D and dispenses the contents into another vessel on the first carousel 102 at point E (e.g., 2-tube dilution processing). In some examples, the second pipetting mechanism 222 aspirates an amount of a first liquid from a container outside of the processing track 100 (e.g., a first reagent), aspirates an amount of a second liquid (e.g., a sample, a diluted sample, a sample and reagent mixture, etc.) from a vessel on the second carousel 104 at point D, and then dispenses both the first and second liquid into a vessel on the first carousel 102 at point E.

In the example shown in FIG. 2, a second wash zone 232 is disposed along the second path of travel 228. The second pipetting mechanism 222 may access the wash zone 232 to clean the second pipette 226 such as, for example, between aspirations of different reagents.

In the example shown in FIG. 2, the analyzer 200 includes a third pipetting mechanism 234. In some examples, the third pipetting mechanism 234 is coupled to the base 208 of the analyzer 200. In the example shown, the third pipetting mechanism 234 is disposed within the bore 132 of the processing track 100 and is also disposed within the first and second diameters 202, 204. In the example shown, the third pipetting mechanism 234 is offset from an axis of rotation of the first and second carousels 102, 104. However, in other examples the third pipetting mechanism is aligned with the axis of rotation. The third pipetting mechanism 234 has multiple degrees of freedom. In the example shown, the third pipetting mechanism 234 has a third probe arm 236 that moves a third pipette 238 along a third path of travel 240 (e.g., a horizontal arc, a range of access) to aspirate/dispense liquid from locations along the third path of travel 240. The third path of travel 240 may be circular, semicircular, linear or a combination thereof. The third pipetting mechanism 234 is also movable in the Z direction (e.g., the vertical direction).

In the example shown, the third pipetting mechanism 234 is positioned to aspirate/dispense from locations (e.g., containers, vessels) disposed along the third path of travel 240. In some examples, the third pipetting mechanism 234 is to aspirate a liquid (e.g., a second reagent) from a container disposed inside the first and second diameters 202, 204 and to dispense the liquid into vessels on the first carousel 102. In some examples, the third pipetting mechanism 234 accesses a container on the third carousel 230. For example, the third pipetting mechanism 234 may access a reagent container on the third carousel 230 at any of the access ports 241*a*, 241*b*, 241*c* located on the third path of travel 240. In some examples, the third carousel 230 includes an inner annular array of containers, such that the third pipetting mechanism 234 can aspirate from these containers. Thus, in some examples, the third pipetting mechanism 234 is a second reagent pipetter and aspirates a second reagent from a container disposed on an inner annular section of the third carousel 230. In the example shown, the third pipetting mechanism 234 can dispense liquid into a vessel on the first carousel 102 at point F. In some examples, the third pipetting mechanism 234 supplies a second reagent to the vessels rotating on the first carousel 102 such as, for example, after the vessels have already been supplied with a sample and a first reagent.

In the example shown, a third wash zone 242 is disposed along the third path of travel 240. The third pipetting mechanism 234 may access to the wash zone 242 to clean the third pipette 238 such as, for example, between aspirations of different reagents.

As shown in FIG. 2, the reader 130 is disposed adjacent to the bore 132 of the housing 106. In the illustrated examples, the reader 130 reads the contents of the vessels as the vessels pass the reader 130. FIG. 2 also illustrates the first and second wash stations 134, 136 and the ITVs 138a-f, discussed above.

As shown in FIGS. 2 and 3, the processing track 100 also includes the first, second, third and fourth diverters 122-128. The first, second and third diverters 122-126 operate to move vessels on the first carousel 102 from one section of a track system 244 to another section of the track system 244 as the vessels rotate on the first carousel 102. In some examples, the diverters 122-128 include solenoids and/or stepper motors. Also, in some examples, the diverters 122-128 include a claw or aligned engagement arms to engage the rim 113a-n of a reaction vessel 112a-n (e.g., below the diverter 122-128) and align the reaction vessel 112a-n in the direction of the desired and/or appropriate track, disclosed in further detail below.

Figure 4A:
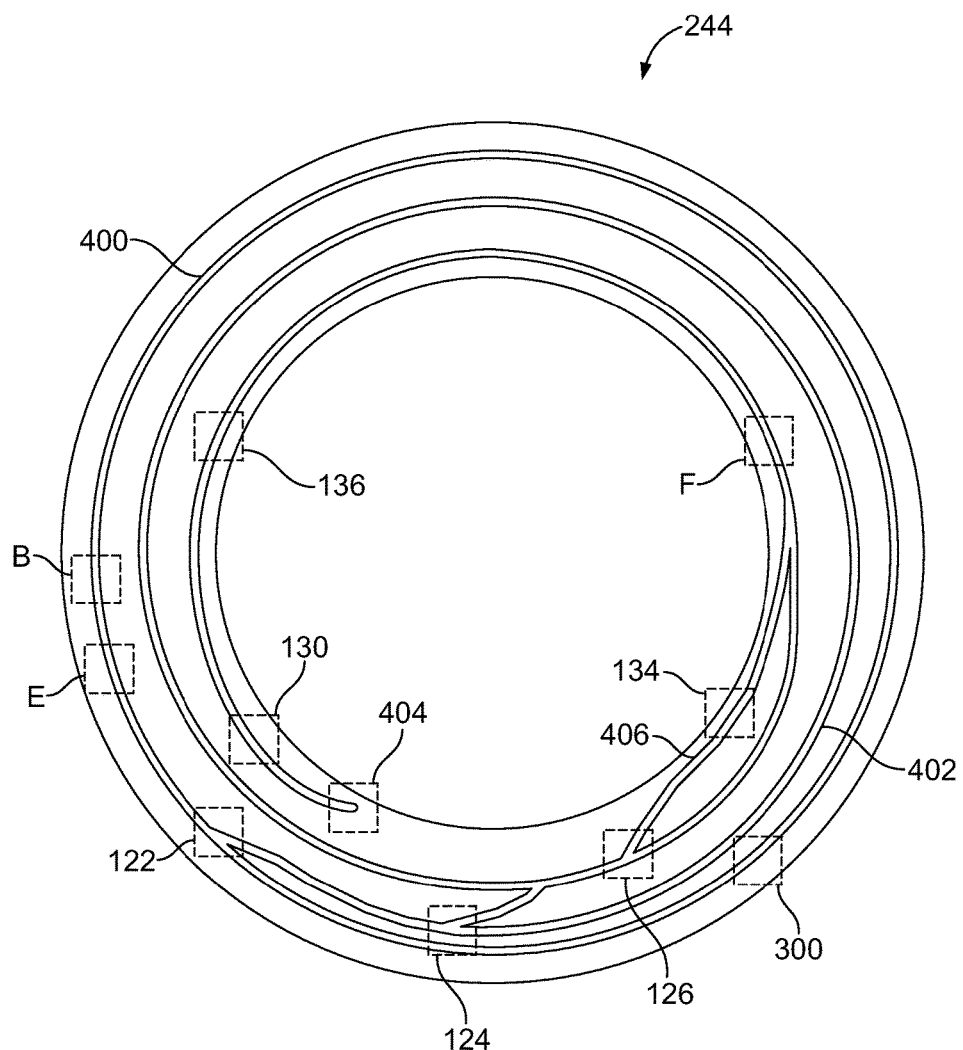
FIG. 4A is a schematic diagram of an example track system utilized in the example processing track of FIG. 1.

A schematic diagram of a top plan view of the track system 244 is illustrated in FIG. 4A. The track system 244 includes a plurality of track sections that are used to align the reaction vessels 112a-n to move along a desired path as the first carousel 102 rotates. In some examples, the track system 244 is disposed above the first carousel 102. In some examples, the track system 244 may be grooved or otherwise formed into a plate or disc that is disposed over the first carousel 102. In other examples, as detailed below, the track system 244 may be grooved or otherwise formed into the bottom of a lid or cover that covers the processing track 100. In such examples, when reaction vessels 112a-n are disposed within the slots 108a-n of the first carousel 102, the rims 113a-n of the reaction vessels 112a-n engage the track system 244 such that as the first carousel 102 rotates with the reaction vessels 112a-n in the slots 108a-n, the reaction vessels 112a-n move (e.g., slide) radially inward and/or outward in their respective slots 108a-n depending the location of the track system 244 and action of the diverters 122-128.

In some examples, the processing track 100 also includes a base comprised of a material such as, for example, aluminum. In some examples the base is disposed below the first carousel 102 within the housing 106. The base may include grooves that match the track system 244 detailed below, such that the bodies of the reaction vessels 112a-n hang within the grooves as the reaction vessels 112a-n rotate. In some examples, the base is thermally conductive and includes heaters to heat the base and, thus, the reaction vessels disposed therein.

In the example shown in FIG. 4A, the track system 244 includes a first track 400 and a second track 402. As shown, the first track 400 forms a continuous circle, and the second track 402 forms a spiral that decreases in diameter in the counterclockwise direction. The relative locations of the first, second, and third diverters 122, 124, 126, points B, E and F, and the first and second wash zones 134, 136 are shown in shadow lines over the track system 244.

In the example shown in FIG. 4A, the area in which the first diverter 122 is disposed includes a junction (e.g., an intersection) where a vessel engaged with the first track 400 can be moved radially inward and, thus, onto the second track 402. In some examples, the first diverter 122 is a clean vessel diverter. For example, a clean vessel may loaded in the outermost area of one of the slots 108a-n on the first carousel 102 with the bottom of the vessel engaged with the first track 400. In some examples, vessels are loaded onto the first and second carousels 102, 104 via a loading mechanism 300 shown in FIG. 3. The area in which the loading mechanism 300 is disposed is shown in dashed lines over the first track 400. As the first carousel 102 rotates in the counterclockwise direction, the vessel stays in the outermost radial area of its slot 108a-n and reaches the area where the first diverter 122 is disposed. In some examples, if the vessel has not been filled with a sample and/or reagent and is considered clean, the first diverter 122 keeps the vessel on the first track 400. Thus, the vessel will continue along the first track 400 and remain in the outermost radial area of its respective slot 108a-n as the first carousel 102 rotates.

In other examples, a first liquid (e.g., a sample) may be added to the vessel at point B via the first pipetting mechanism 206 and/or a second liquid (e.g., a first reagent) may be added to the vessel at point E via the second pipetting mechanism 222 as the first carousel 102 rotates the vessel clockwise along the first track 400. In such an example, if the contents of the vessel are ready for further processing (e.g., a sample and a reagent have been added to the vessel), the first diverter 122 can divert the vessel from the first track 400 onto the second track 402. In such an example, as the first carousel 102 rotates, the vessel moves radially inward in its respective slot 108a-n as the second track 402 decreases in diameter around the counterclockwise direction. In the example shown, the second track 402 completes two rotations between the area of the first diverter 122 and an unload area 404 (e.g., a passive unloader) where the vessel may be removed from the first carousel 102.

In the example shown in FIG. 4A, the area of the reader 130 (shown in FIGS. 1-3) is shown in dashed lines over on the track system 244. The reader 130 is disposed in a location such that the reader 130 can read vessels that are on the second track 402 passing by the reader 130 such as, for example, the vessels positioned along the innermost area of the carousel on the section of the track 402 leading to the unload area 404. Therefore, in the example shown, the reader 130 analyzes the contents of a vessel before the vessel is unloaded from the first carousel 102 at the unload area 404.

In the illustrated example, a vessel moving from the first track 400 onto the second track 402 slides radially inwards in its respective slot 108a-n on the first carousel 102, which leaves the outer position of the slot 108a-n vacant. Therefore, in some examples, another vessel may be loaded into the outer position of the same slot 108a-n and be engaged with the first track 400.

In the example shown, the point F is disposed on the second track 402. In some examples, once a vessel has been engaged with the second track 402, another liquid (e.g., a second reagent) may be added to the vessel at point F via the third pipetting mechanism 234.

In an example processing operation, a sample may be added to a vessel on the first track 400 at point B. As the carousel rotates, the vessel reaches point E and, if desired, a reagent and/or other liquids may be added to the vessel. The first diverter 122 may divert the vessel onto the second track 402, and the vessel continues around the second track 402. As the first carousel 102 rotates, the vessel reaches point F, where a second reagent may be added to the vessel. The vessel continues to travel along the second track 402 and, at the location of the reader 130, the contents of the reaction vessel are read.

In the example shown in FIG. 4A, the area where the second diverter 124 is disposed includes another junction (e.g., an intersection, a spur, a side track, a subtrack) that connects an outer section (e.g., an earlier section) of the second track 402 with an inner section (e.g., a later section) of the second track 402. As shown, the second track 402 forms a spiral that makes about two rotations. However, a vessel traveling on the second track 402 may be diverted by the second diverter 124 and moved onto another section of the second track 402 about one rotation ahead. Thus, the second diverter 124 is a stat diverter that accelerates the progress of a vessel along the second track 402. For example, certain sample(s) and reagents react faster than others, and less time is needed to conduct a complete test. In these examples, the reaction is ready for reading before two rotations on the second track 402. Therefore, instead of making two rotations on the second track 402 before reaching the reader 130, the second diverter 124 may divert a vessel inward to bypass a portion of the second track 402 (e.g., skip one rotation of the second track 402) and, thus, reduce time before the reading the reaction. However, other tests require a longer time to react and can be kept on the main path of the second track 402 to follow a longer path before the reading.

As mentioned above, the example processing track 100 also includes two wash zones 134, 136. As shown in the example in FIG. 4A, the area in which the third diverter 126 is disposed includes a connection point (e.g., a spur, a side track, a subtrack) that connects the second track 402 to a wash zone side track 406. The wash zone side track 406 leads to the area of the first wash zone 134. Some example tests require an additional wash to remove unwanted conjugate and other materials from reaction mixture. Therefore, if desired, a vessel moving along the second track 402 may be diverted by the third diverter 126 onto the wash zone side track 406. The wash zone side track 406 reconnects to the second track 402 before the area of point F, where another liquid (e.g., a second reagent) may be added to a vessel. As shown, the second wash zone 136 is disposed over a section of the second track 402 prior to the reader 130. Thus, a vessel may go through two wash zones 134, 136 before a reading.

In some examples, the first and second carousels 102, 104 rotate in intervals or locksteps during a diagnostic test. Each interval or lockstep has an advancement step during which the carousel moves (e.g., indexes) and a stop step during which the carousel is idle. During the idle stop step, a plurality of functions may occur to the vessels on the first and second carousels 102, 104 such as, for example, dispensing sample, dispensing reagent, washing the contents of a reaction vessels, reading the contents of a reaction vessel, mixing the contents of a reaction vessel, etc. Depending on the type of diagnostic test performed, the carousels 102, 104 may have different lockstep times.

In some examples, the first carousel 102 has a lockstep time (the combination of an advancement step and a stop step) of about 18 seconds (i.e., the first carousel 102 rotates or indexes incrementally to a different position about every 18 seconds). During the advancement step of the lockstep, the first carousel 102 moves (e.g., translates, indexes, etc.) one position in the counterclockwise direction (e.g., one position is the distance between the center of one slot to the center of the next slot). In other examples, the second carousel 104 may rotate more or less depending on the scheduling protocols designed for the specific analyzer and/or for a particular diagnostic testing protocol. In some examples, the advancement step of the first carousel 102 may take place during about less than one second (e.g., 400 milliseconds (ms)) of the 18 second lockstep, and the first carousel 102 may remain idle (e.g., stationary) for about 17 seconds during the stop step of the lockstep. During these 17 seconds, the first, second and third pipetting mechanisms 206, 222, 234 aspirate and/or dispense liquids (e.g., simultaneously or in sequence), including any microparticles contained therein, and other functional modules (e.g., the reader 130, the first and second wash zones 134, 136, the ITVs 138a-e, etc.) operate around the carousels 102, 104. In some examples, some of the functional modules also operate during the advancement step of a lockstep. In other examples, the advancement and stop times may be different.

In an example operation, a vessel 112a is loaded into the slot 108a of the first carousel 102 and is positioned in the outer section of the slot 108a to engage first track 400 of the track system 244 (e.g., via the loading mechanism 300). The first carousel 102 moves through a plurality of locksteps, incrementally moving (e.g., indexing) the vessel 112a one position at a time in the counterclockwise direction. The vessel 112a reaches point B and, during this lockstep, the first pipetting mechanism 206 aspirates a liquid (e.g., a sample) and dispenses the liquid into the vessel 112a. During the next lockstep, the first carousel 102 rotates, and the vessel 112a is indexed one position counterclockwise to point E and, during this lockstep the second pipetting mechanism 222 aspirates a second liquid (e.g., a first reagent) and dispenses the liquid into the vessel 112a. The first carousel 102 continues indexing one position every lockstep. When the vessel 112a reaches the first diverter 122, the vessel 112a is directed radially inward onto the second track 402 as described above. The vessel 112a continues around the first carousel 102 on the second track 402 and moves radially inward within the slot 108a. If desired, the second and third diverters 124, 126 may divert the vessel 112a to different sections of the second track 402, as detailed above. When the vessel 112a reaches point F, another liquid (e.g., a second reagent) is aspirated, via the third pipetting mechanism 234 and dispensed into the vessel 112a. The vessel 112a continues to rotate incrementally on the first carousel 102 and passes the reader 130, where a reading is taken. When the test is complete, the vessel 112a is unloaded at the unloading area 404.

In some examples, the processing track 100 is used for immunoassays and one or more of the reagents added to the vessel may include paramagnetic microparticles. In such examples, the first and/or second wash zone 134, 136, may be used for magnetic microparticle processing, where a plurality of wash steps and magnetic processing steps are used to separate parts of the test sample desired for reading.

As noted above, in some examples, the second carousel 104 also has a total lockstep time of about 18 seconds. In some examples, the carousel 104 has a two-stage lockstep, and each lockstep of the second carousel 104 includes a major lockstep and minor lockstep. Each of the major lockstep and the minor lockstep includes an advancement step and a stop step. In some examples, the major lockstep is about 16 seconds and the minor lockstep is about 2 seconds. In other examples, the timing may be changed to suit the type of testing performed. The two-stage lockstep enables a reaction vessel on the second carousel 104 to be filled with a sample and a reagent, which occur at different positions (e.g., one position apart), during one lockstep of the first carousel 102 and, thus, prepared for pretreatment incubation. In some examples, the minor lockstep occurs when a reaction vessel receives a sample (e.g., at point A) and the major lockstep occurs when the reaction vessel receives a reagent (e.g., point D). During the major lockstep, reagent may be dispensed in the reaction vessel, the contents of the reaction vessel may be diluted and/or the contents or portions of the content of the reaction vessel may be aspirated and transferred to a reaction vessel on the main processing carousel. Thus, having a two-stage lockstep sequence allows a reaction vessel on the pretreatment carousel to be prepared, which occurs at two positions, and allows the reaction vessel sufficient time for reagent dispensing and aspiration which, in some examples, involves multiple processing steps.

As an example implementation of a two-stage lockstep, a vessel 112a is deposited into one of the slots 110a-n on the second carousel 104 with the loading mechanism 300 shown in FIGS. 3 and 4. The second carousel 104 goes through multiple two-stage locksteps of alternating major and minor locksteps. In some examples, the vessel 112a is located at one position clockwise from point A (FIG. 2) during a major lockstep. During the next minor lockstep, the second carousel 104 rotates one position in the counterclockwise direction such that the vessel 112a is now located at point A and held stationary. During this time (e.g., two seconds), the first pipetting mechanism 206 may aspirate a liquid (e.g., a sample) and dispense the liquid into the vessel 112a. Then, during the next major lockstep, the second carousel 104 again rotates one position in the counterclockwise direction such that the vessel 112a is now at point D and held stationary. During this time (e.g., sixteen seconds), the second pipetting mechanism 222 aspirates another liquid (e.g., a first reagent) and dispenses the liquid into the vessel 112a. Then, during a second minor lockstep, the second carousel 104 rotates in the counterclockwise direction and again moves the vessel 112a one more position. A second major lockstep follows. This alternating sequence of minor and major locksteps may continue, and the vessel 112a is rotated around the second carousel 104.

In some examples, when the vessel 112a reaches point C, the contents of the vessel 112a may be aspirated, via the first pipetting mechanism 206, and dispensed into another vessel on the first carousel 102 at point B. Such an example may be used for the purposes of incubating a sample prior to placing sample on the first carousel 102 for processing. By mixing a sample and reagent in the vessel on the second carousel 104, the reaction has time to incubate prior to placement in a vessel on the first carousel 102 and, thus, the overall processing time of the vessels on the first carousel 102 is decreased. After the contents or a portion of the contents of the reaction vessel are aspirated at point C, the second carousel 104 continues through more locksteps and the empty, near-empty or otherwise used vessel 112a is rotated in the counterclockwise direction. However, during this second rotation of the vessel 112a, the vessel 112a encounters point A during a major lockstep and point D during a minor lockstep. During this time, no functions are performed on the vessel 112a. The vessel 112a continues to rotate on the second carousel 104 and reaches the fourth diverter 128 (e.g., an active unloader) and is unloaded from its slot 110a-n on the second carousel 104. When the slot 110a-n reaches the loading mechanism 300, another clean vessel may be loaded in the slot 110a-n. Thus, in this example, the processing cycle of a given vessel on the second carousel 104 is about two full rotations. Therefore, in some examples, every other vessel on the second carousel 104 is going through the same sequencing as the vessel two slots in front or behind of that slot.

As another example (e.g., a two-tube dilution processing sequence), a vessel 112a is deposited into one of the slots 110a-n on the second carousel 104 with the loading mechanism 300 shown in FIGS. 3 and 4. The second carousel 104 goes through multiple two-stage locksteps of alternating major and minor locksteps. When the vessel 112a reaches point A, during a minor lockstep, a sample may be dispensed into the vessel 112a. During the next major lockstep, the vessel 112a is rotated to point D and a dilution reagent is added to the vessel 112a via the second pipetting mechanism 222. The dilution reagent dilutes the sample in the reaction vessel. In some examples, the second pipetting mechanism 222, during this same lockstep, aspirates another reagent from an outside container, aspirates some of the diluted sample/reagent mixture from the reaction vessel at point D, and the dispense mixture of the second reagent and the diluted sample/reagent mixture into a reaction vessel on the first carousel 102 at point E for processing.

The second carousel 104 continues to rotate the vessel 112a through a plurality of major and minor locksteps. In some examples, the vessel 112a continues to rotate on the second carousel 104 and reaches the fourth diverter 128 (e.g., an active unloader) and is unloaded from its slot 110a-n on the second carousel 104. When the slot 110a-n reaches the loading mechanism 300, another clean vessel may be loaded in the slot 110a-n. Thus, in this example, the processing cycle of a given vessel on the second carousel 104 is about one rotation. In other examples, the empty reaction vessel may be rotated around the second carousel 104 another rotation until the vessel reaches the fourth diverter 128.

Figure 4B:
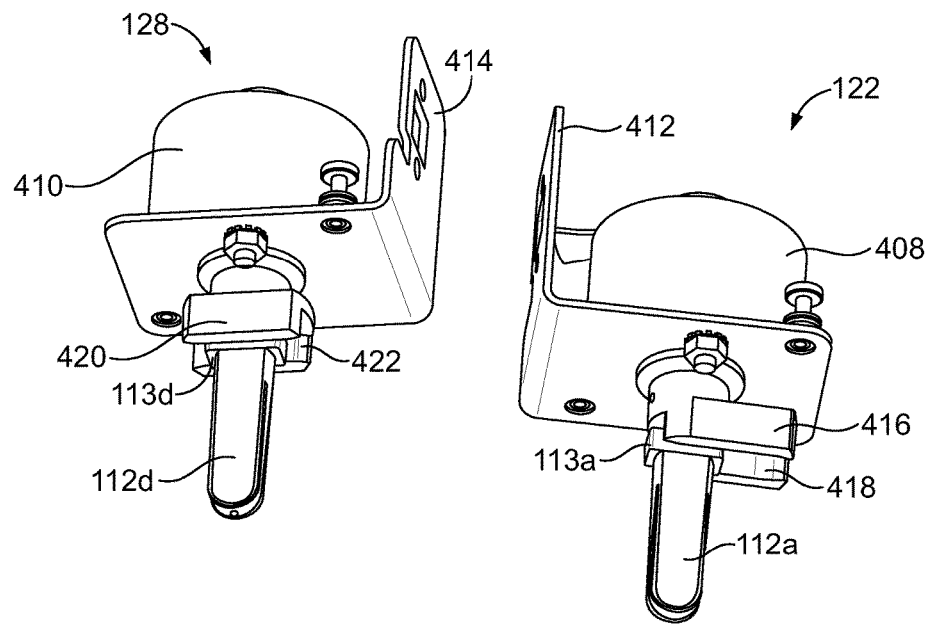
FIG. 4B illustrates a perspective view from the bottom of example diverters utilized with the example processing track of FIG. 1 and engaged with example reaction vessels.
Figure 4C:
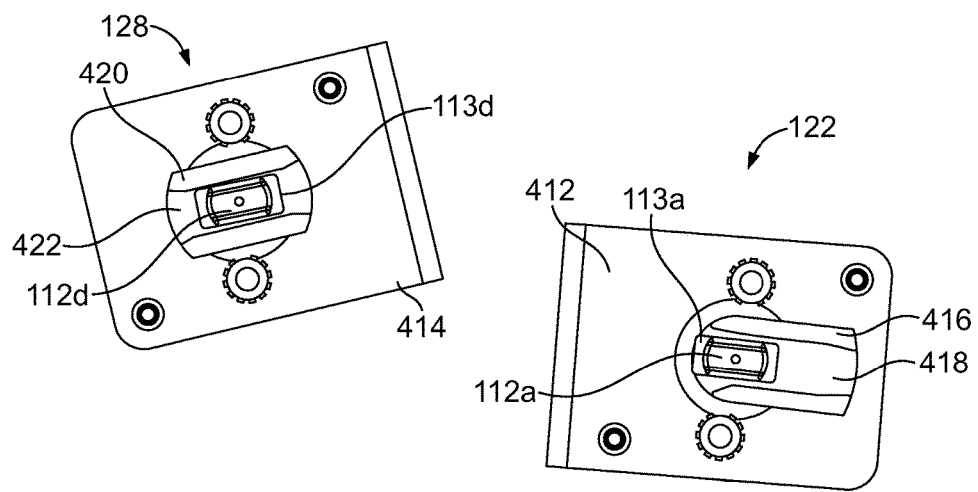
FIG. 4C illustrates a bottom view of the example diverters of FIG. 4B.

FIGS. 4B and 4C illustrate examples of the first diverter 122 and the fourth diverter 128. In some examples, the second and third diverters 124, 126 are similar to the first diverter 122 and, thus, will include similar components. In the example shown, the first and fourth diverters 122, 128 include respective motors 408, 410 and respective mounting brackets 412, 414. In some examples, the motors 408, 410 are solenoids, stepper motors or servo motors. The mounting brackets 412, 414 may be used to mount the first and fourth diverters 122, 128 to, for example, the housing 106 (FIG. 1), a cover 424 (FIGS. 4D and 4E detailed below), the analyzer 200 (FIG. 2) and/or another surface of an example analyzer.

In the example shown, the first diverter 122 includes a first paddle 416 (e.g., a claw and/or aligned engagement arms) with a first channel 418. In the illustrated example, a reaction vessel 112a is engaged in the first paddle 416. A top rim 113a of the reaction vessel 112a is to slide through the first channel 418 of the first paddle 416. For example, when the reaction vessel passes 112a underneath the first diverter 122, the top rim 113a slides into the first channel 418 of the first paddle 416. If the first diverter 122 is to divert the direction of the reaction vessel 112a, the first paddle 416 is rotated (e.g., clockwise, counterclockwise) via the first motor 408 to align the first channel 418 and the reaction vessel 112a in a different direction to direct the reaction vessel 112a onto a chosen track. In some examples, the first carousel 102 indexes in a plurality of locksteps, each lockstep having an advancement step and a stop step. In some examples, the reaction vessel 112a is indexed during the advancement step into the position shown in FIG. 4B where the top rim 113a of the reaction vessel 112a is engaged with the first paddle 416. During the stop step, or idle period, the first motor 408 rotates the first paddle 416 to align the top rim 113a of the reaction vessel 112a in a desired direction with an appropriate track. During the next advancement step, the reaction vessel 112a is indexed forward one position and, thus, the top rim 113a of the reaction vessel 112a is moved out of the first channel 418 of the first paddle 416 and along the desired track. In some examples, the first diverter 122 rotates the first paddle 416 between about 30° to about 35°.

In the example shown, the fourth diverter 128 includes a fourth paddle 420 (e.g., a claw and/or aligned engagement arms) with a fourth channel 422. In the illustrated example, a reaction vessel 112d is engaged in the fourth paddle 420. A top rim 113d of the reaction vessel 112d is to slide through the fourth channel 422 of the fourth paddle 420. For example, when the reaction vessel 112d passes underneath the fourth diverter 128, the top rim 113d slides into the fourth channel 422 of the fourth paddle 420. If the fourth diverter 128 is to unload or divert the direction of the reaction vessel 112d, the fourth paddle 420 is rotated via the fourth motor 410. When rotated, the fourth channel 422 of the fourth paddle 422 is aligned in a different direction to direct the reaction vessel 112d onto another track or off the second carousel 104. In some examples, the second carousel 104 indexes in a plurality of locksteps, each lockstep having an advancement step and a stop step. In some examples, the reaction vessel 112d is indexed during the advancement step into the position shown in FIG. 4B. During the stop step, or idle period, the fourth diverter 128 rotates the fourth paddle 420, which rotates the reaction vessel 112d. In some examples, the reaction vessel 112d is supported in its respective slot 110a-n by the top rim 113d and the fourth diverter 128 rotates the reaction vessel 112d until the rim 113d of the reaction vessel 112d is not supported by the second carousel 104 and falls through the slot 110a-n (e.g., into a waste module). In some examples, the fourth diverter 128 rotates the fourth paddle 420 about 90°.

Figure 4D:
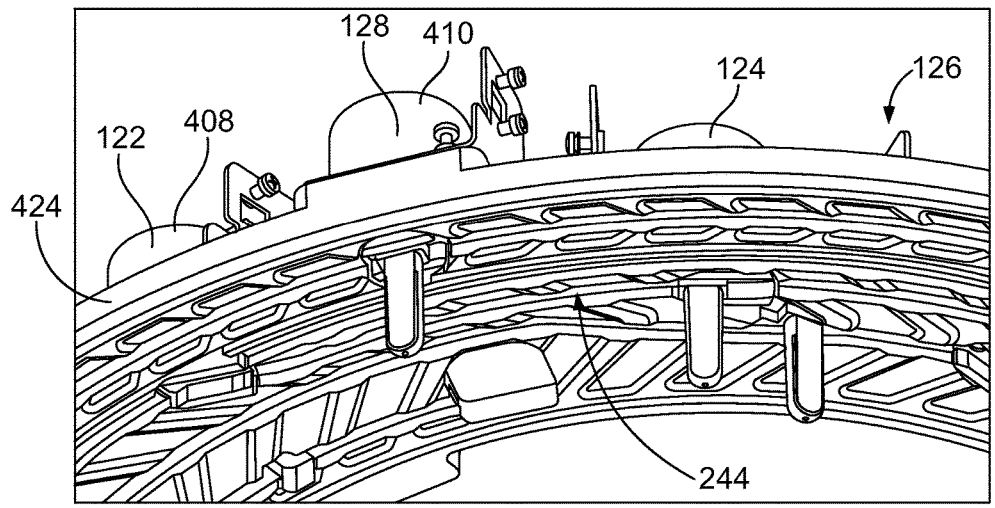
FIG. 4D illustrates a perspective view from the bottom an example cover having the example track system of FIG. 4A and the example diverters of FIGS. 4B and 4C.
Figure 4E:
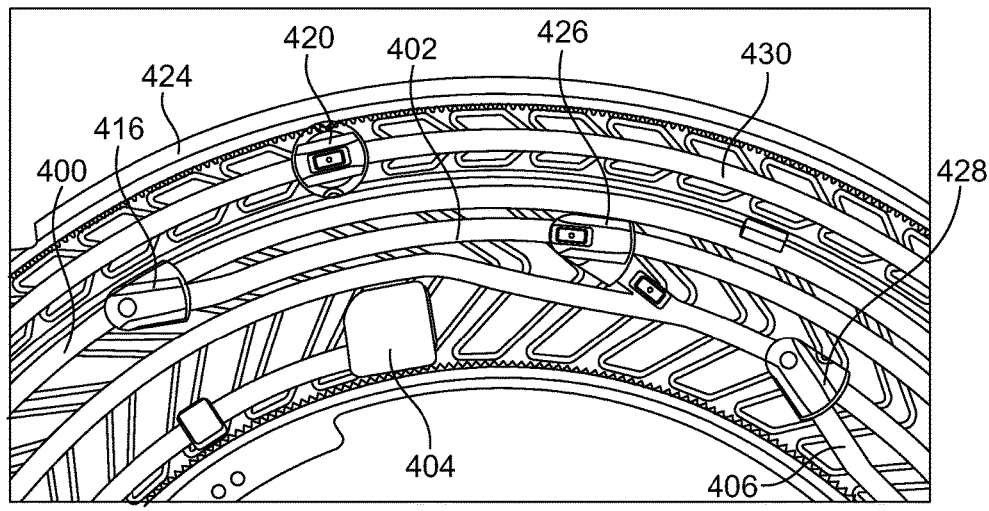
FIG. 4E illustrates a bottom view of the example cover and the example diverters of FIG. 4D.

FIGS. 4D and 4E illustrate an example cover 424 (e.g., a lid, a cap) that may be used to cover the first and second carousel 102, 104 of the example processing track 100. As shown, the track system 244 is disposed on the bottom on the bottom of the cover 424. In some examples, the track system 244 is grooved or otherwise formed into the bottom of the lid 424. In the example shown, the first, second, third and fourth diverters 122, 124, 126, 128 are disposed on top of the cover 424 and their respective paddles extend through the cover 424 and into the track system 244 disclosed above.

In the example shown, the first and second carousels 102, 104 have been removed for clarity to view the bottom of the cover 424 and the track system 244. In some examples, the top rims 113a-n of the respective vessels 112a-n rest on the carousels 102, 104 when the reaction vessels 112a-n are disposed within the slots 108a-n, 110a-n of the respective carousels. When placed in the first plurality of slots 108a-n, the tops 113a-n of the respective reaction vessels 112a-n are disposed within the groove of the track system 244 and, thus, travel along the respective paths of the track system 244. As the first carousel 102 indexes, the first, second, third diverters 122, 124, 126 operate to direct the reaction vessels 112a-n, as disclosed above.

As shown in FIG. 4E, the first paddle 416 of the first diverter 122 operates to direct reaction vessel 112a-n between the first track 400 and the second track 402. A second paddle 426 is coupled to the second diverter 124 and diverts reaction vessels 112a-n from one area (e.g., section, portion, location) on the second track 402 to another area on the second track 402. Also shown, a third paddle 428 coupled to the third diverter 126 operates to divert the reaction vessels 112a-n from the second track 402 on to the wash zone side track 406. In the example shown, a third track 430 is disposed on the bottom of the cover 424 and similarly directs the reactions vessels 112a-n on the second carousel 104. The fourth paddle 420 of the fourth diverter 128 operates to remove reaction vessels 112a-n from the second carousel 104, as detailed above.

Figure 5A:
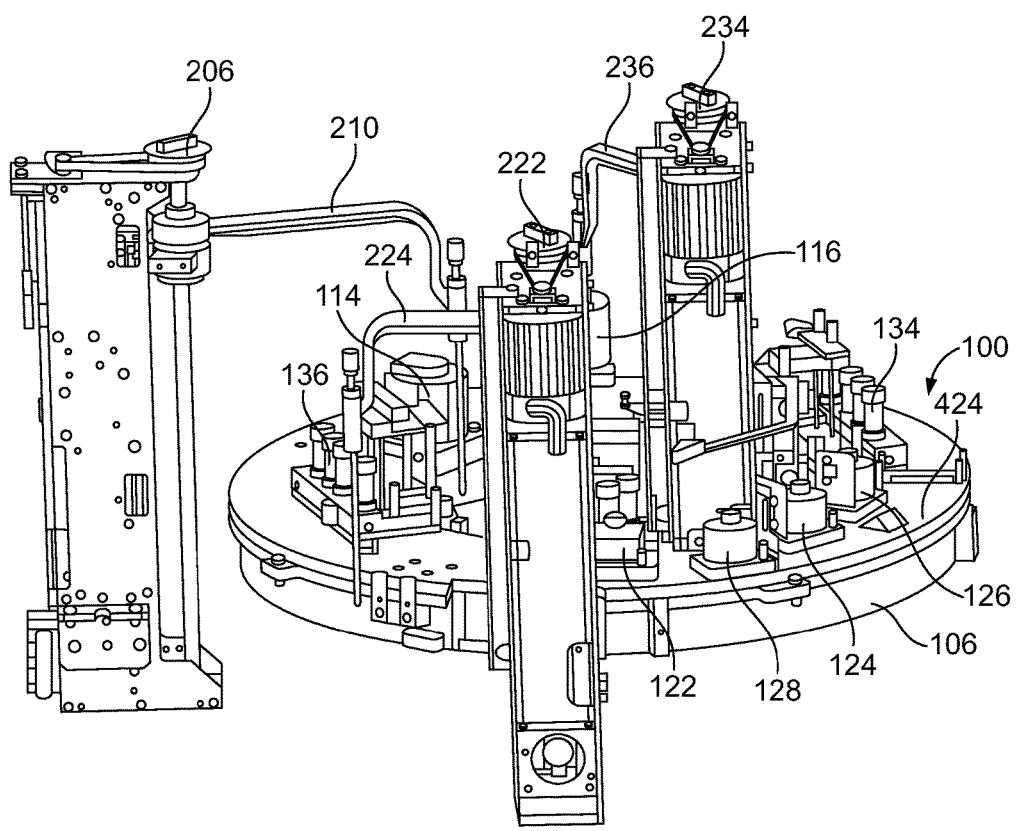
FIG. 5A illustrates a perspective view of the example processing track of FIG. 1 and example pipetting mechanisms.
Figure 5B:
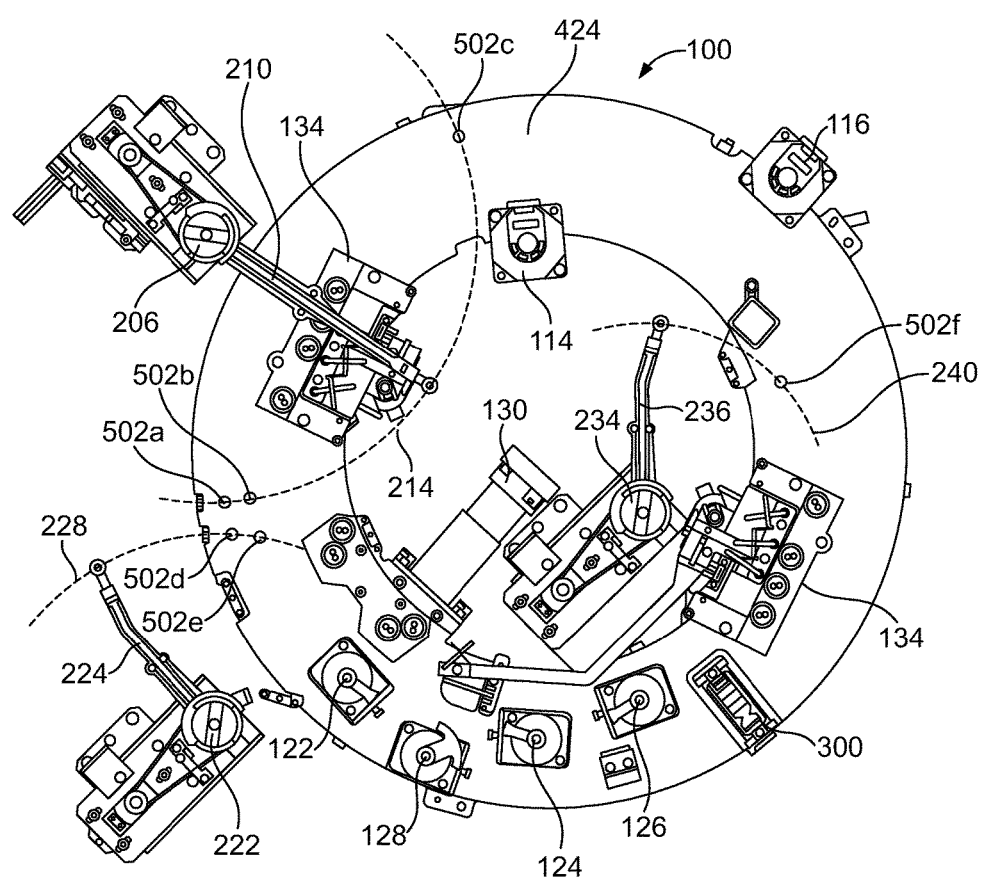
FIG. 5B illustrates a top plan view of the example processing track and pipetting mechanisms of FIG. 5A.
Figure 5C:
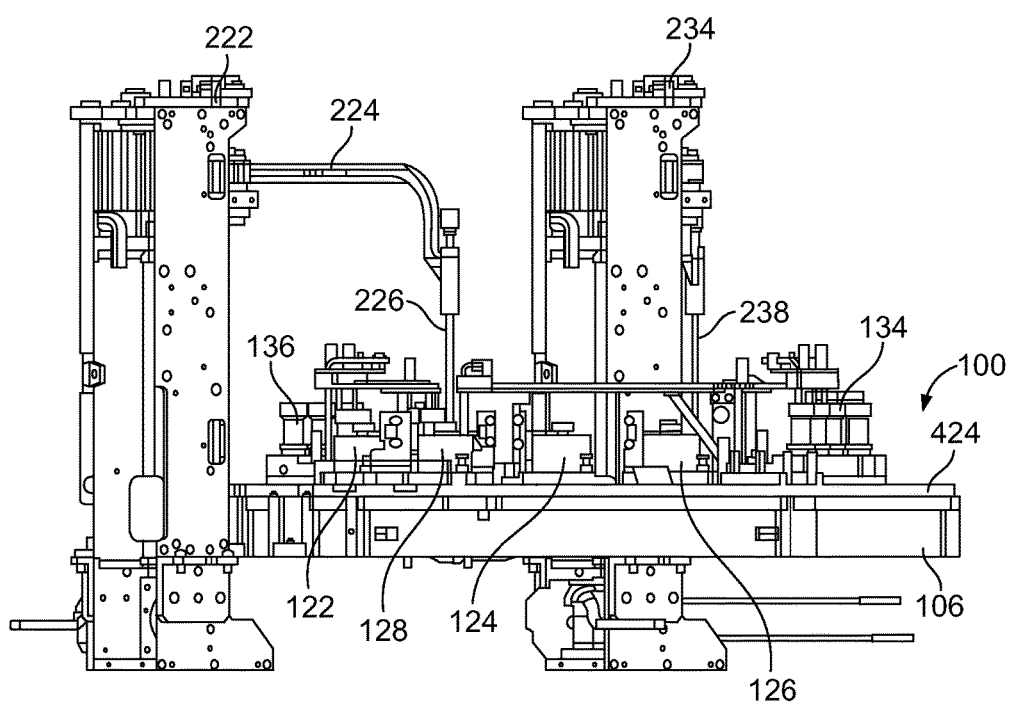
FIG. 5C illustrates a front side view of the example processing track and pipetting mechanisms of FIG. 5A.

FIGS. 5A, 5B and 5C illustrate different views of the processing track 100 and the pipetting mechanisms 206, 222, 234 shown in FIGS. 1-4. Specifically, FIG. 5A is a perspective view, FIG. 5B illustrates a top plan view, and FIG. 5C illustrates a front side view. The various components have been labeled in accordance with the number detailed above.

As shown in FIGS. 5A, 5B and 5C, the processing track 100 includes the cover 424 to contain the first and second carousels 102, 104 (FIGS. 1-3). In some examples, the first, second, third and fourth diverters 122-128 are coupled to the lid 500 and interact with the vessels rotating below the cover 424 on the first and second carousels 102, 104. As shown in FIG. 5B, a plurality of apertures 502a-f (e.g., openings, holes, gaps, etc.) are formed in the cover 424 such that the pipettes 212, 226, 238 of the pipetting mechanism 206, 222, 234 may access the vessels on the first and second carousels 102, 104 through the cover 424. Specifically, the apertures 502a, 502b and 502c are disposed along the first path of travel 214 of the first pipetting mechanism 206 and align with points A, B and C as shown in FIGS. 1-4. Apertures 502d and 502e are disposed along the second path of travel 228 of the second pipetting mechanism 222 and align with points D and E as shown in FIGS. 1-4. In addition, aperture 502f is disposed along the third path of travel 240 of the third pipetting mechanism 234 and is aligned with point F as shown in FIGS. 1-4.

Figure 6:
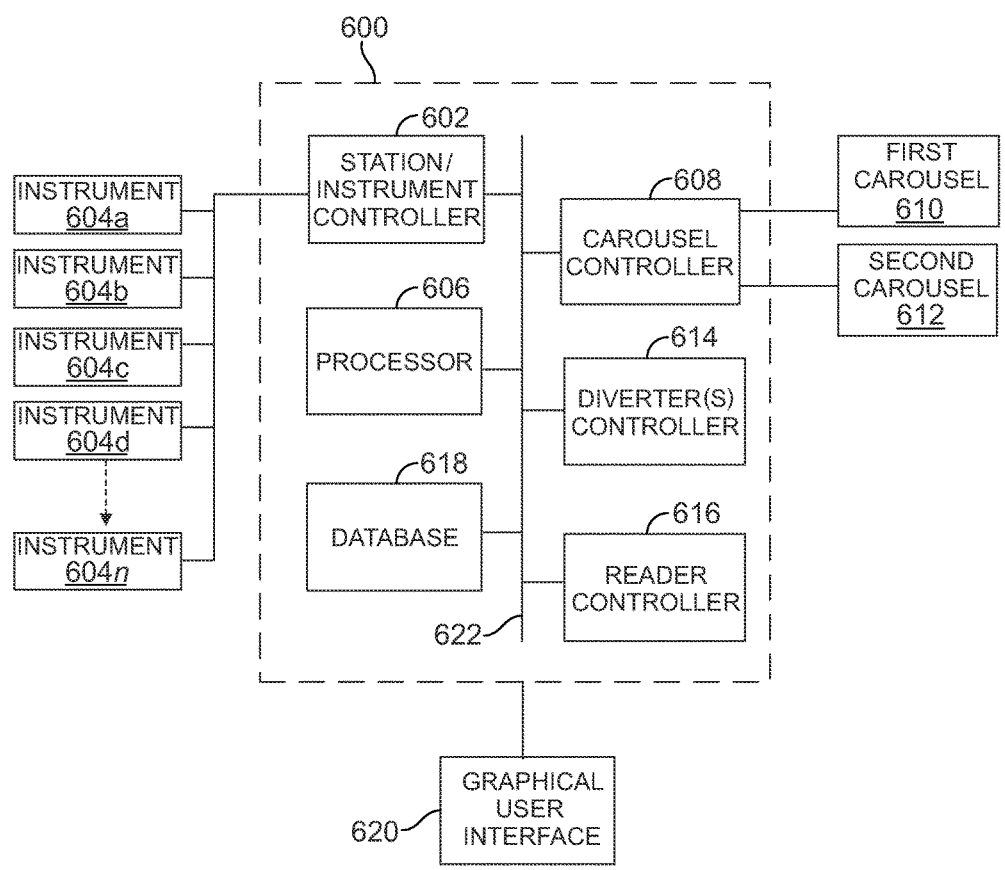
FIG. 6 is a block diagram of an example processing system for the example analyzer and/or the example processing track shown in FIGS. 1-5C.

FIG. 6 is a block diagram of an example processing system 600 for use with an automated diagnostic analyzer such as, for example, the analyzer 200 including the example processing track 100 disclosed above. The example processing system 600 includes a station/instrument controller 602, which controls the instruments and mechanisms used during a diagnostic test. In the example shown, the station/instrument controller 602 is communicatively coupled to instruments 604a-n. The instruments 604a-n may include, for example, components of the example analyzer 200 disclosed above including the first, second and/or third pipetting mechanisms 206, 222, 234, one or more of the ITVs 138a-f, the first and/or second wash zones 134, 136, the loading mechanism 300 and/or the reader 130. The example processing system 600 includes an example processor 606 that operates the station/instrument controller 602 and, thus, the instruments 604a-n in accordance with a schedule or testing protocol as disclosed herein.

The example processing system 600 also includes a carousel controller 608, which controls one or more carousels of the analyzer. In the example shown, the carousel controller 608 is communicatively coupled to a first carousel 610 and a second carousel 612. The first carousel 610 and the second carousel 612 may correspond, for example, to the first and second carousels 102, 104 disclosed above in connection with the example processing track 100. The carousel controller 608 controls the rotation of the first and second carousels 610, 612, such as, for example, using a motor (e.g., the motors 114, 116 disclosed in connection with the analyzer 200 and the processing track 100). Also, the example processor 606 operates the carousel controller 608 and, thus, the carousels 610, 612 in accordance with a schedule or testing protocol.

The example processing system 600 also includes a diverter controller 614, which controls one or more diverters of the analyzer. In some examples, one or more of the carousels 610, 612 includes a plurality of elongated slots to hold one or more vessels for conducting a diagnostic test. A track system may be disposed below one of the carousels 610, 612 to lead the vessels of that carousel radially inward or outward to perform certain functions on the vessels. In some examples, diverters may be used to divert vessels on one of the carousels 610, 612, from one section of a track to another section of a track. In the example analyzer 200 and processing track 100 disclosed above, the first diverter 122 diverts a vessel from the first track 400 to the second track 402, the second diverter 124 diverts a vessel from one section of the second track 402 to another section of the second track 402, the third diverter 126 diverts a vessels onto the wash zone side track 406, and the fourth diverter 128 unloads a vessels from the second carousel 104. The diverter controller 614 in the example processing system 600 may be used to control the diverters (e.g., the diverter motors) of the example processing track 100.

The example processing system 600 includes a reader controller 616 that operates to control when the readings are taken. In some examples, a reader (e.g., the reader 130) is disposed along the inside or the outside of one of the carousels 610, 612, such that as the carousel rotates, the reader may analyze the contents of the respective vessels on the carousel. In some examples, a reaction vessel is held stationary in front of the reader for a predetermined time and a reading is taken. In other examples, one or more reaction vessels may be passed by the reader, and the reader takes a plurality of individual readings corresponding to each reaction vessel as the reaction vessels pass.

The example processing system 600 also includes a database 618 that may store information related to the operation of the example system 600. The information may include, for example, the testing protocol, reagent identification information, reagent volume information, sample identification information, position information related to a position (e.g., reaction vessel, lockstep and/or rotation) of a sample, status information related to the contents and/or position of a reaction vessel, pipette position information, carousel position information, lockstep duration information, pretreatment timing information, etc.

The example processing system 600 also includes a user interface such as, for example, a graphical user interface (GUI) 620. An operator or technician interacts with the processing system 600 and, thus, the analyzer 200 and/or the processing track 100 via the interface 620 to provide, for example, commands related to the testing protocols, information related to the samples to be tested, information related to the reagents or other fluids to be used in the testing, etc. The interface 620 may also be used by the operator to obtain information related to the status and/or results of any testing completed and/or in progress.

In the example shown, the processing system components 602, 606, 608, 614, 616, 618 are communicatively coupled to other components of the example system 600 via communication links 622. The communication links 622 may be any type of wired connection (e.g., a databus, a USB connection, etc.) and/or any type of wireless communication (e.g., radio frequency, infrared, etc.) using any past, present or future communication protocol (e.g., Bluetooth, USB 2.0, USB 3.0, etc.). Also, the components of the example system 600 may be integrated in one device or distributed over two or more devices.

While an example manner of implementing the processing track 100 and/or the analyzer 200 of FIGS. 1-5C is illustrated in FIG. 6, one or more of the elements, processes and/or devices illustrated in FIG. 6 may be combined, divided, re-arranged, omitted, eliminated and/or implemented in any other way. Further, the example station/instrument controller 602, the example instruments 604a-n, the example processor 606, the example carousel controller 608, the example first carousel 610, the example second carousel 612, the example diverter controller 614, the example reader controller 616, the example database 618, the example graphical user interface 620 and/or, more generally, the example processing system 600 of FIG. 6 may be implemented by hardware, software, firmware and/or any combination of hardware, software and/or firmware. Thus, for example, any of the example station/instrument controller 602, the example instruments 604a-n, the example processor 606, the example carousel controller 608, the example first carousel 610, the example second carousel 612, the example diverter controller 614, the example reader controller 616, the example database 618, the example graphical user interface 620 and/or, more generally, the example processing system 600 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example station/instrument controller 602, the example instruments 604a-n, the example processor 606, the example carousel controller 608, the example first carousel 610, the example second carousel 612, the example diverter controller 614, the example reader controller 616, the example database 618, the example graphical user interface 620 is/are hereby expressly defined to include a tangible computer readable storage device or storage disk such as a memory, a digital versatile disk (DVD), a compact disk (CD), a Blu-ray disk, etc. storing the software and/or firmware. Further still, the example processing system 600 of FIG. 6 may include one or more elements, processes and/or devices in addition to, or instead of, those illustrated in FIG. 6, and/or may include more than one of any or all of the illustrated elements, processes and devices.

Flowcharts representative of example methods 700, 800 and 900 for implementing the processing track 100, the analyzer 100 and/or the processing system 600 of FIGS. 1-6 are shown in FIGS. 7-9B. In this example, the methods may be implemented as machine readable instructions comprising a program for execution by a processor such as the processor 1012 shown in the example processor platform 1000 discussed below in connection with FIG. 10. The program may be embodied in software stored on a tangible computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowcharts illustrated in FIGS. 7-9B, many other methods of implementing the example processing track 100, the example analyzer 200 and/or the example processing system 600 may alternatively be used. For example, the order of execution of the blocks may be changed, and/or some of the blocks described may be changed, eliminated, or combined.

As mentioned above, the example processes 700, 800 and 900 of FIGS. 7-9B may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals. As used herein, "tangible computer readable storage medium" and "tangible machine readable storage medium" are used interchangeably. Additionally or alternatively, the example processes 700, 800 and 900 of FIGS. 7-9B may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable device or disk and to exclude propagating signals. As used herein, when the phrase "at least" is used as the transition term in a preamble of a claim, it is open-ended in the same manner as the term "comprising" is open ended.

Figure 7:
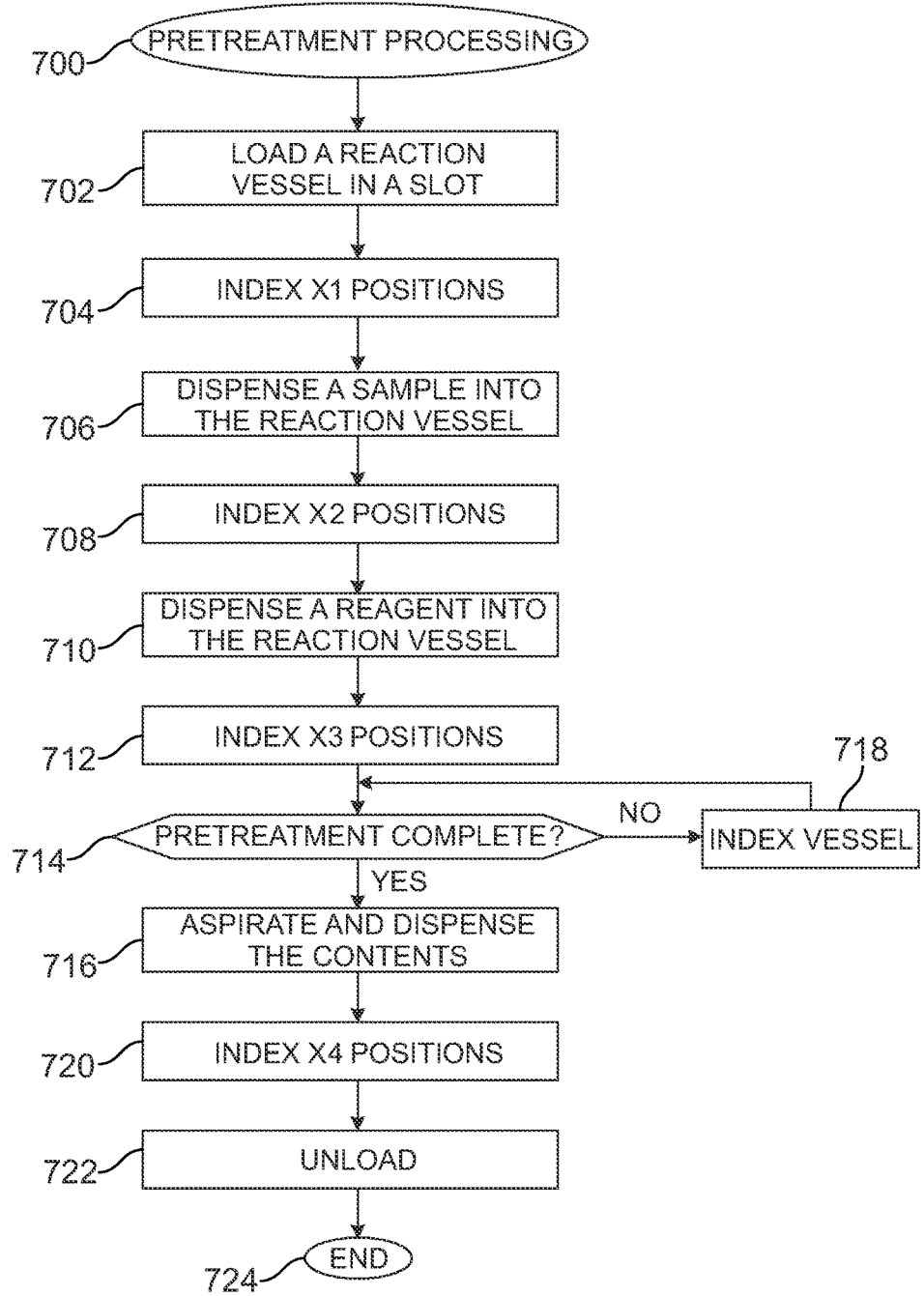
FIG. 7 is a flowchart illustrating an example pretreatment process.

FIG. 7 illustrates the example process 700 for diagnostic testing, which may be implemented, for example, by the example processing track 100, the example analyzer 200, and/or the example processing system 600 disclosed herein. The example process 700 is described from the perspective of the operations for a single vessel as the vessel rotates on a carousel of an analyzer throughout multiple locksteps. More specifically, the example process 700 may be used, for example, for pretreating or preparing a sample prior to being loaded onto a main processing carousel or processing path. The example pretreatment operations may be used, for example, in a clinical chemistry test or an immunoassay test. Example analyzers and/or processing tracks disclosed herein include a pretreatment carousel (e.g., the second carousel 104) having a plurality of slots for receiving a plurality of reaction vessels. One or more reaction vessels on the pretreatment carousel may be used to incubate a sample with a reagent and/or perform other pretreatment functions to decrease the testing duration of a processing carousel (e.g., the first carousel 102) where the reactions are to be analyzed.

The example process 700 includes loading a reaction vessel in a slot (block 702) on the pretreatment carousel. In some examples, a loader is disposed above and/or adjacent to the pretreatment carousel and is used to load reaction vessels into the slots of the pretreatment carousel. In the example processing track 100 disclosed above, the loading mechanism 300 (FIGS. 3 and 4) is used to load the reaction vessels into the slots 110a-n on the second carousel 104.

The example process 700 includes indexing the reaction vessel X1 positions (block 704). In some examples, the pretreatment carousel rotates in a plurality of locksteps. During each lockstep, the pretreatment carousel indexes one position forward and remains idle for a period of time. During the period of time when the carousel is idle, different diagnostic testing functions may be performed on the reaction vessels on the pretreatment carousel. In some examples, not all of the locksteps are the same duration. In some such examples, the pretreatment carousel indexes in an alternating major and minor lockstep arrangement, where, for example, the major lockstep has a longer idle time than the minor lockstep. In some examples, X1 represents the number of locksteps or index positions between the position at which the reaction vessel was loaded and the position in which a sample is added to the reaction vessel. In the example processing track 100 disclosed above, the second carousel 104 is indexed one position in the counterclockwise direction during each lockstep. In some examples, if a reaction vessel is loaded at the loading mechanism 300 (FIGS. 3 and 4), the reaction vessel is indexed 41 positions until the reaction vessel reaches point A where, for example, a sample may be added to the reaction vessel via the first pipetting mechanism 206. Therefore, in some examples, X1 is set to 41.

The example process also includes dispensing a sample into the reaction vessel (block 706). In some examples, a sample pipette is disposed near the pretreatment carousel to dispense sample(s) into the reaction vessel(s) on the pretreatment carousel. In the example processing track 100 disclosed above, the first pipetting mechanism 206 is disposed outside of the processing track 100. In some examples, the first pipetting mechanism 206 is to aspirate a sample from a sample container disposed along the first path of travel 214 and to dispense the sample into a reaction vessel on the second carousel 104 at point A.

The example process 700 includes indexing the reaction vessel X2 positions (block 708). In some examples, X2 represents the number of locksteps or index positions between the position at which sample is dispensed into the reaction vessel and the position at which a reagent is dispensed into the reaction vessel. In the example processing track 100 disclosed above, the second carousel 104 is indexed one position in the counterclockwise direction during each lockstep. In some examples, if a reaction vessel on the second carousel 104 is loaded with sample at point A, the reaction vessel is indexed only one position until point D, where, in some examples, a reagent may be dispensed into the reaction vessel. Therefore, in some examples, X2 is set to one.

The example process 700 includes dispensing a reagent into the reaction vessel (block 710). In some examples, a first reagent pipette is disposed near the pretreatment carousel to dispense a first reagent into the reaction vessels on the pretreatment carousel. If the reaction vessel is not in position to receive a reagent and/or no reagent is otherwise to be dispensed into the reaction vessel, no reagent is added and the reaction vessel is indexed another position. The reaction vessel continues to index on the pretreatment carousel until the reaction vessel reaches the position where the first reagent pipette can and is scheduled to dispense a first reagent into the reaction vessel (block 710). In the example analyzer 200 and processing track 100 disclosed above, the second pipetting mechanism 222 may be used for dispensing a reagent into a reaction vessel on the second carousel 104 at point D. In the example shown in FIGS. 2-4, a reaction vessel loaded on to the second carousel 104 at the loading mechanism 300 is about 42 index positions in the counterclockwise direction away from point D, and, one index position from point A. Once a reaction vessel reaches point D, a first reagent may be dispensed into the reaction vessel (block 710). In some examples, this step occurs during a major lockstep to provide sufficient time for aspirating and dispensing.

The example process 700 includes indexing the reaction vessel X3 positions (block 712). In some examples, X3 represents the number of locksteps or index positions from the position at which the reagent is added to the reaction vessel and a position at which the contents or a portion of the contents of the reaction vessel are to be aspirated out of the reaction vessel. In some examples, a certain amount of reacting time is desired to ensure the sample and the reagent have reacted or at least reacted a desired amount. In such examples, X3 may be correlated with the number of locksteps (and time) desired to allow the reagent to react with the sample. In the example processing track 100 disclosed above, the second carousel 104 is indexed one position in the counterclockwise direction during each lockstep. In some examples, after receiving a reagent at point D, a reaction vessel is indexed a number of times until point C, where, for example, the sample and reagent mixture, or a portion thereof, may be aspirated out of the reaction vessel. In some examples, X3 is set to 46, which is the number of index positions from point D to point C in the counterclockwise direction.

The example process 700 includes determining if pretreatment is complete (block 714). If pretreatment is complete, the example process 700 include aspirating the contents or a portion of the contents of the reaction vessel and dispensing the contents or portion thereof into a reaction vessel on the main processing carousel (block 716). In some examples, the sample pipette, that is disposed near the pretreatment carousel, is to aspirate the pretreated mixture from the reaction vessel and to dispense the mixture into a vessel on the main processing carousel. In other examples, a different pipette mechanism may be used to aspirate the contents of the reaction vessel and dispense the contents into a reaction vessel on the main processing carousel. In the examples shown in FIGS. 2-4, a reaction vessel that was previously at point D, and received reagent, will index 46 positions in the counterclockwise direction until the reaction vessel reaches point C. When the reaction vessel reaches point C, the first pipetting mechanism 206 may aspirate the contents of the reaction vessel and dispense the contents into a vessel on the first carousel 102 at point B for processing on the first carousel 102.

If the pretreatment is not complete (block 714), the reaction mixture is not aspirated from the reaction vessel and the reaction vessel is indexed (block 718). The reaction vessel continues to index (block 718) on the pretreatment carousel until the pretreatment is complete (block 714), and the reaction vessel reaches a position where the sample pipette can and is scheduled to aspirate the mixture from the reaction vessel and dispense the mixture into a vessel on the regular processing path (block 716).

The example process 700 includes indexing the reaction vessel X4 positions (block 720). In some examples, X4 represents the number of locksteps or index positions from the position at which the contents of the reaction vessel were removed for processing and the position at which the reaction vessel is unloaded. In the example processing track 100 disclosed above, the second carousel 104 is indexed one position in the counterclockwise direction during each lockstep. In some examples, the fourth diverter 128 is to remove reaction vessels (when scheduled to) from the second carousel 104. In some examples, X4 is set to 24, which is the number of index positions from point C to the location of the fourth diverter 128. In this example, the reaction vessel passes through points A and D again, but during this rotation, no sample or reagent is added.

The example process 700 includes unloading the reaction vessel (block 722). In some examples, a diverter or unloader is position above and/or adjacent the pretreatment carousel and is to unload reaction vessels when scheduled to (e.g., after the pretreated contents or portions thereof have be aspirated out for processing). Once the reaction vessel is unloaded, the example process 700 ends (block 724) for that reaction vessel. In the example processing track 100 disclosed above, the fourth diverter 128 is to remove reaction vessels from the second carousel after the pretreated contents of such reaction vessel or portions thereof have been removed for processing. In some examples, the fourth diverter 128 includes the fourth paddle 420 that engages a rim 113a-n of a reaction vessel 112a-n beneath the fourth diverter 128. In some examples, the fourth diverter 128 rotates the reaction vessel 112a-n such that the rim 113a-n of the reaction vessel is no longer supported on the second carousel 104 and, thus, unloads the reaction vessel 112a-n from the second carousel 104. In some examples, the fourth diverter 128 unloads (e.g., by rotating) the reaction vessel 112a-n during the advancement step of a lockstep. In some examples, the fourth diverter 128 has a rotational range of about 90°.

After the reaction vessel is unloaded, the second carousel 104 continues to index and another reaction vessel (e.g., a clean reaction vessel) may be deposited or loaded (block 702) into the same slot previously occupied by the unloaded reaction vessel. The clean reaction vessel may be added when the slot reaches the loading mechanism 300, and another example process 700 may begin. Thus, in this example processing track 100, the processing cycle of a reaction vessel on the second carousel 104 is about two rotations (i.e., from the position at which the reaction vessel is deposited into a slot till the position at which the reaction vessel is unloaded). During the first rotation a reaction vessel is loaded into a slot and sample and reagent are added to the reaction vessel, and during the second rotation the contents are aspirated from the reaction vessel, and the reaction vessel is unloaded.

Additionally, this example is viewed from the perspective of one reaction vessel progressing through pretreatment operations on a pretreatment carousel. However, multiple other pretreatment reactions may be occurring simultaneously during the same indexes in the other slots of the pretreatment carousel and may also be performed using the process 700.

Figure 8:
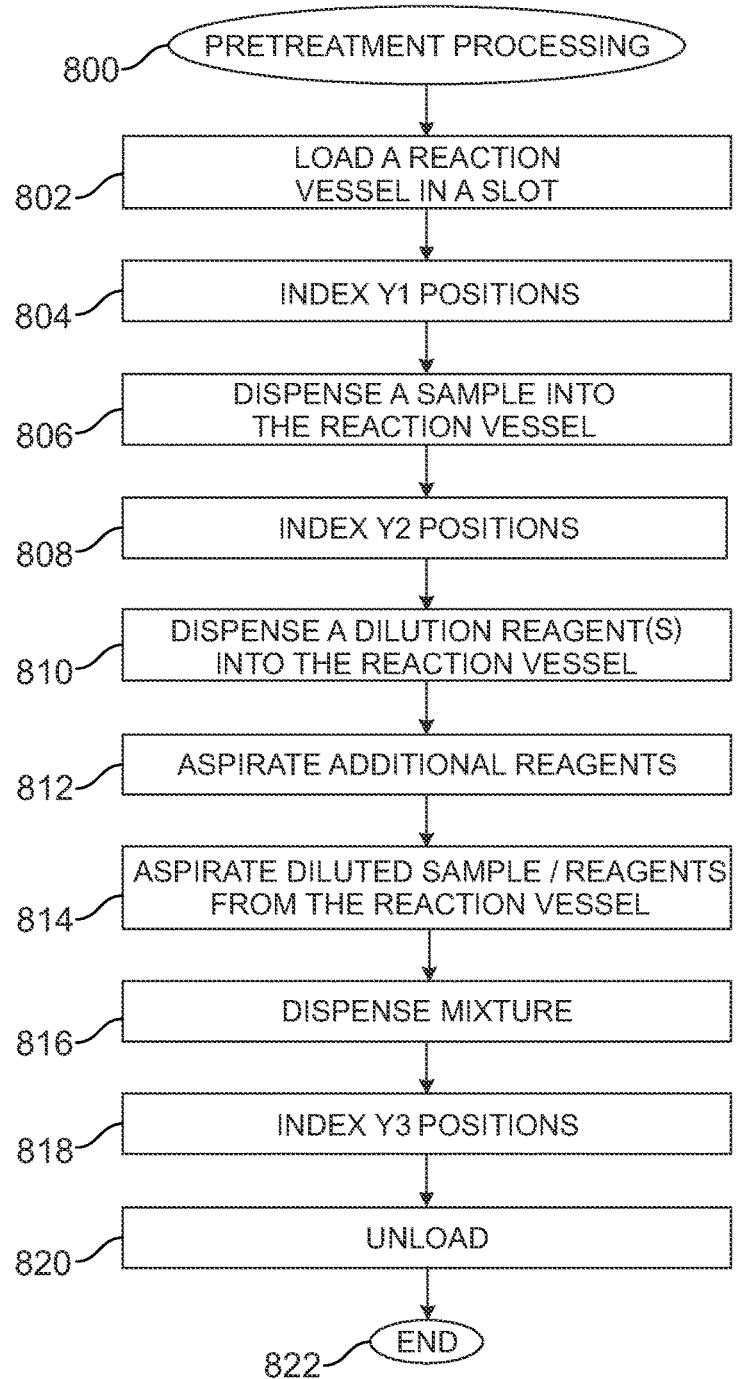
FIG. 8 is a flowchart illustrating another example pretreatment process.

FIG. 8 illustrates another example process 800 for diagnostic testing, which may be implemented, for example, by the example processing track 100, the example analyzer 200, and/or the example processing system 600 disclosed herein. The example process 800 is described from the perspective of the operations for a single vessel as the vessel rotates on a carousel of an analyzer throughout multiple locksteps. More specifically, the example process 800 may be used, for example, for preparing or pretreating a sample prior to being transferred to a processing carousel for analysis. The example pretreatment operations may be used, for example, in a clinical chemistry test or an immunoassay test. Example analyzers and/or processing tracks disclosed herein include a pretreatment carousel (e.g., the second carousel 104) having a plurality of slots for receiving a plurality of reaction vessels. Some diagnostic testing protocols involve a two-tube dilution processing sequence in which a reagent and a diluted sample are mixed. Therefore, one or more reaction vessels on the pretreatment carousel may be used for mixing and aspirating a reagent and a diluted sample to prepare the sample and reagent mixture for testing on the main processing carousel (e.g., the first carousel 102) where the reactions are to be analyzed. Performance of the dilution pretreatment process on the pretreatment carousel 104 decreases processing time on the main processing carousel 102.

The example process 800 includes loading a reaction vessel in a slot (block 802) on the pretreatment carousel. In some examples, a loader is disposed above and/or adjacent to the pretreatment carousel and is used to load reaction vessels into the slots of the pretreatment carousel. In the example processing track 100 disclosed above, the loading mechanism 300 (FIGS. 3 and 4) is used to load the reaction vessels into the slots 110a-n on the second carousel 104.

The example process 800 includes indexing the reaction vessel Y1 positions (block 804). In some examples, the pretreatment carousel rotates in a plurality of locksteps in the counterclockwise direction. During each lockstep, the pretreatment carousel indexes one position forward and remains idle for a period of time. During the period of time when the carousel is idle, different diagnostic testing functions may be performed on the reaction vessels on the pretreatment carousel. In some examples, not all of the locksteps are the same duration. In some such examples, the pretreatment carousel indexes in an alternating major and minor lockstep arrangement, where, for example, the major lockstep has a longer idle time than the minor lockstep. In some examples, Y1 represents the number of locksteps or index positions between the position at which the reaction vessel was loaded and the position at which a sample is added to the reaction vessel. In some examples, if a reaction vessel is loaded at the loading mechanism 300 (FIGS. 3 and 4), the reaction vessel is indexed 41 positions till point A where, for example, a sample may be added to the reaction vessel via the first pipetting mechanism 206. Therefore, in some examples, Y1 is set to 41.

The example process 800 includes dispensing a sample into the reaction vessel (block 806). In some examples, a sample pipette is disposed near the pretreatment carousel to dispense sample into the reaction vessels on the pretreatment carousel. In the example processing track 100 disclosed above, the first pipetting mechanism 206 is disposed outside of the processing track 100. In some examples, the first pipetting mechanism 206 is to aspirate a sample from a sample container disposed along the first path of travel 214 and to dispense the sample into a reaction vessel on the second carousel 104 at point A. In the example shown in FIGS. 2-4, a reaction vessel loaded on to the second carousel 104 by the loading mechanism 300 is about 41 index positions in the counterclockwise direction away from point A. When the reaction vessel reaches point A, sample may be dispensed into the reaction vessel via the first pipetting mechanism 206.

The example process 800 also includes indexing the reaction vessel Y2 positions (block 808). In some examples, Y2 represents the number of locksteps or index positions between the position at which sample is dispensed into the reaction vessel and the position at which a reagent or other liquid is dispensed into the reaction vessel. In some examples, if a reaction vessel on the second carousel 104 is loaded with sample at point A, the reaction vessel is indexed only one position until point D, where, in some examples, a reagent and/or other liquids may be dispensed into the reaction vessel. Thus, in some examples, Y2 is set to one.

The example process 800 also includes dispensing a dilution reagent(s) into the reaction vessel (810). In some examples, a reagent pipette is disposed near the pretreatment carousel to dispense a first dilution reagent into the reaction vessels on the pretreatment carousel. In the example analyzer 200 and processing track 100 disclosed above, the second pipetting mechanism 222 may be used for dispensing a dilution reagent into a reaction vessel on the second carousel 104 at point D. In the example shown in FIGS. 2-4, a reaction vessel loaded on to the second carousel 104 at the loading mechanism 300 is about 42 index positions in the counterclockwise direction away from point A. However, if the reaction vessel was at point A, then the reaction vessel is one index position away from point D. When a reaction vessel reaches point D, a dilution reagent may be dispensed into the reaction vessel.

The example process 800 also includes aspirating an additional reagent (block 812). In some examples, after the reagent pipette has dispensed dilution reagent into the reaction vessel, the reagent pipette is to aspirate another reagent from a different container. In the example processing track 100 disclosed above, the second pipetting mechanism 222 may aspirate a reagent from, for example, a reagent container on the third carousel 230.

The example process 800 includes aspirating the diluted sample/reagents from the reaction vessel (block 814). Therefore, the reagent pipette will have aspirated from both the reagent container and the reaction vessel containing the diluted sample/reagent mixture. In the example analyzer 200 and processing track 100 disclosed above, the second pipetting mechanism 222 may be used for aspirating a second reagent after the second pippetting mechanism 222 has dispensed the first dilution reagent into the reaction vessel. The second pipetting mechanism 222 may then aspirate the contents (i.e., the diluted sample mixture) of the reaction vessel at point D on the second carousel 104.

The example process 800 includes dispensing the mixture of the second reagent and the diluted sample into a reaction vessel on the processing carousel (block 816). The reagent pipette may be used to dispense the diluted sample and reagent mixture into a vessel on the processing carousel for processing. In the example analyzer 200 and processing track 100 disclosed above, the second pipetting mechanism 222 may dispense this mixture into a reaction vessel on the first carousel 102 at point E. In some examples, this step occurs during a major lockstep to provide sufficient time for aspirating and dispensing.

The example process 800 includes indexing the reaction vessel Y3 positions (block 818) via, for example, indexing processes disclosed herein. In some examples, Y3 represents the number of locksteps or index positions from the position at which the diluted sample mixture or a portion thereof was removed for processing and the position at which the reaction vessel is unloaded. In some examples, the fourth diverter 128 is to remove reaction vessels (when scheduled to) from the second carousel 104. In such an example, Y3 may be set to eight, which is the number of index positions from point D to the location of the fourth diverter 128.

The example process 800 also includes unloading the reaction vessel from the pretreatment carousel (block 820). In some examples, a diverter or passive unloader is disposed adjacent the pretreatment carousel and is to unload reaction vessels when a reaction vessel reaches the diverter and is scheduled to be unloaded (e.g., after aspiration of the pretreated mixture). When the reaction vessel is unloaded, the example process 800 ends (block 822) for that reaction vessel. After the reaction vessel is unloaded, the second carousel 104 continues to index and another reaction vessel (e.g., a clean reaction vessel) may be deposited or loaded (block 802) into the same slot previously occupied by the unloaded vessel. The clean vessel may be added when the slot reaches the loading mechanism 300, and the example process 800 may start over.

This example testing is viewed from the perspective of one reaction vessel progressing through pretreatment operations on a pretreatment carousel. However, multiple other pretreatment reactions may be occurring simultaneously during the same indexes in the other slots of the pretreatment carousel and may be performed using this process as well.

Figure 9A:
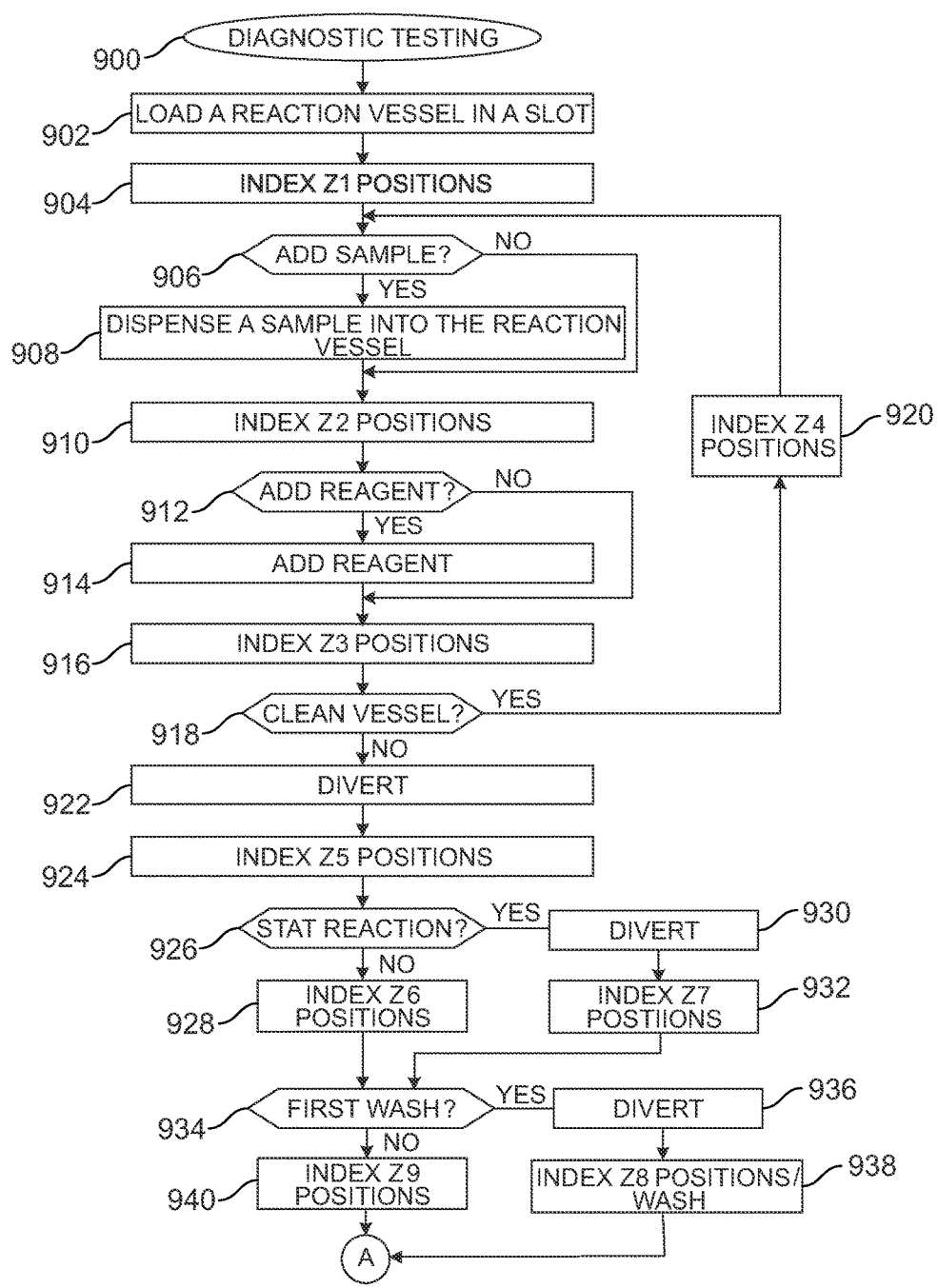
FIG. 9A is a flowchart illustrating an example diagnostic testing process.
Figure 9B:
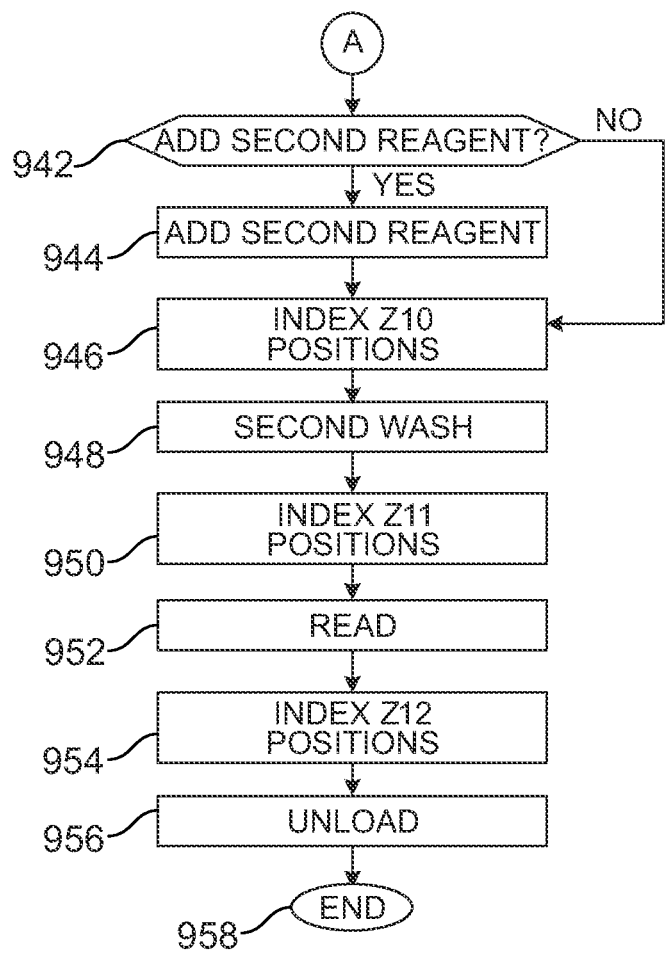
FIG. 9B is a continuation of the flowchart of FIG. 9A.

FIGS. 9A and 9B illustrate an example diagnostic testing process 900, which may be implemented, for example, by the example processing track 100, the example analyzer 200, and/or the example processing system 600 disclosed herein. The example process 900 is described from the perspective of the operations for a single vessel as the vessel rotates on a processing carousel of an analyzer throughout multiple locksteps. The example diagnostic testing operations may be used, for example, in a clinical chemistry test or an immunoassay test. Example analyzers and/or processing tracks disclosed herein include a processing carousel (e.g., the first carousel 102) having a plurality of slots for receiving a plurality of reaction vessels. In some examples, the processing carousel rotates in locksteps (e.g., discrete intervals). In some examples, each lockstep includes an advancement step and a stop step. During the advancement step, the reaction vessels on the processing carousel are indexed (e.g., moved) one position forward (e.g., counterclockwise) from respective previous positions. In some examples, the processing carousel includes 46 slots for receiving reaction vessels.

The example process 900 includes loading a reaction vessel in a slot (block 902) on the processing carousel. In some examples, the slots of the processing carousel are elongated such that a reaction vessel in one of the slots can move radially inward and outward in the slot. In some examples, the processing carousel includes a track system disposed above or below the process carousel. In some examples the track system includes a plurality of indentations or grooves on a lid or cover of the analyzer, and rims of the respective reaction vessels engage the grooves and, thus, follow the path of the track system. In the example processing track 100 disclosed above, the loading mechanism 300 is disposed above the first carousel 102 to load reaction vessels into the slots 108a-n of the first carousel 102. The reaction vessels are deposited in the outermost radial area of the slot 108a-n and engage the first track 400 of the track system 244 once loaded.

The example process 900 includes indexing the reaction vessel Z1 positions (block 904). In some examples, Z1 may represent the number of locksteps or index positions between the position at which the reaction vessel is loaded and the position at which at which a sample is added to the reaction vessel. In the example processing track 100 disclosed above, the first carousel 102 is indexed one position in the counterclockwise direction during each lockstep. In some examples, if a reaction vessel is loaded at the loading mechanism 300 (FIGS. 3 and 4), the reaction vessel is indexed 31 positions until point B where, for example, a sample may be added to the reaction vessel via the first pipetting mechanism 206. Therefore, in some examples, Z1 is set to 31. The example process 900 includes determining whether a sample is to be dispensed into the reaction vessel (block 906). In some examples, a sample pipette is disposed near the processing carousel to dispense sample into the reaction vessel on the processing carousel. In some examples, a sample is aspirated from a sample container. In other examples, the sample may be a pretreated sample and may be aspirated from the pretreatment carousel as disclosed in block 716 of the example pretreatment process 700 in FIG. 7. In other examples, a first reagent pipette may be used to aspirate reagent and a diluted sample/reagent from the pretreatment carousel as disclosed in the example two-tube dilution process disclosed in the process 800 of FIG. 8. If the reaction vessel is in a position to receive a sample and is scheduled to receive a sample, then a sample is dispensed into the reaction vessel (block 908). If the reaction vessel is not in position to receive a sample or is not scheduled to receive a sample, no sample or diluted sample mixture is added.

In the example analyzer 200 and processing track 100 disclosed above, the first pipetting mechanism 206 may be used for dispensing a sample into a reaction vessel on the first carousel 102 at point B. In some examples, the first pipetting mechanism 206 aspirates a sample from a sample container disposed outside of the processing track 100 and dispenses the sample into a reaction vessel on the first carousel at point B. In other examples, the first pipetting mechanism 206 aspirates a pretreated sample from a reaction vessel on the second carousel 104 at point C and dispenses this mixture into the reaction vessel on the first carousel 102 at point B. In other examples, the second pipetting mechanism 222 aspirates a reagent and a diluted sample/reagent mixture from the second carousel 104 at point D and dispenses the reagent and mixture into a reaction vessel on the first carousel 102 at point E.

After a sample is added (block 908) or if no sample is to be added (block 906), the example process 900 includes indexing the reaction vessel Z2 positions (block 910). In some examples, Z2 represents the number of locksteps or index positions from the position at which the reaction vessel is to receive sample and a position at which the reaction vessel is to receive a reagent. In the example processing track 100 disclosed above, a reaction vessel at point B indexes one position to point E, where, in some examples, a reagent is added to the reaction vessel. Therefore, in some examples, Z2 is set to one.

The example process 900 includes determining if a reagent is to be added to the reaction vessel (block 912). In some examples, a first reagent pipette is disposed near the processing carousel to dispense a first reagent into the reaction vessels on the processing carousel. If the reaction vessel is in a position to receive a reagent and is scheduled to receive a reagent, the first reagent pipette will aspirate a reagent from a reagent container and dispense the reagent into the reaction vessel (block 914). If the reaction vessel is not in position to receive a first reagent and/or is not scheduled to receive the first reagent, no reagent is added.

In the example analyzer 200 and processing track 100 disclosed above, the second pipetting mechanism 222 may be used for dispensing a reagent into a reaction vessel on the first carousel 102 at point E. During the positions prior to point E, a reaction vessel is indexed and held idle or stationary (i.e., no reagent is dispensed into the reaction vessel). In the examples shown in FIGS. 2-4, if the reaction vessel was at point B, then the reaction vessel is one index position away from point E. Once a reaction vessel reaches point E, a first reagent may be dispensed into the reaction vessel.

After a reagent is added (block 914) or if no reagent is to be added (block 912), the example process 900 includes indexing the reaction vessel Z3 positions (block 916). In some examples, Z3 represents the number of locksteps or index positions between the positions (or time) at which the first reagent was added to the reaction vessel and the time the reaction vessel reaches a first diverter, which may divert the reaction vessel onto a spiral track portion of the track system. The example processing track 100 disclosed above includes the first diverter 122 which may divert a reaction vessel from the first track 400 to the second track 402. In such an example, the number of locksteps or index positions from point E to the location of the first diverter 122 is four. Therefore, in some examples, Z3 is set to four.

The example process 900 includes determining if the reaction vessel is clean (block 918). If the reaction vessel is clean such as, for example, if no samples or reagents were dispensed into the reaction vessel, and the reaction vessel is not ready for processing, the reaction vessel is indexed Z4 positions (block 920). In such examples, the reaction vessel is maintained on an outer track of the track system and, thus, in the outermost radial area of the respective slot. In some examples, Z4 represents the number of locksteps or positions until the reaction vessel is in the position where the reaction vessel may receive a sample (block 906). In the example processing track 100 disclosed above, if a reaction vessel is clean (e.g., not used), the reaction vessel remains on the first track 400 and continues rotating in the outermost section of its slot such that during the next rotation, the reaction vessel passes through points B and E, where control of the example process 900 returns to block 906 and the reaction vessel may receive, for example, a sample and a reagent.

If the vessel is not clean (e.g., includes a sample and a reagent and is ready for processing) (block 918), the reaction vessel is diverted (block 922) onto a second track (e.g., a spiral track). In the example processing track 100 disclosed above, the first diverter 122 diverts reaction vessels from the first track 400 to the second track 402 to continue the diagnostic testing.

After the reaction vessel is diverted to the second track, the example process 900 includes indexing the reaction vessel Z5 positions (block 924). In some examples, Z5 represents the number of locksteps between the first diverter (when the reaction vessel was diverted onto the second track) and a second diverter (block 926) (e.g., the stat diverter). In some examples, the second track spirals around the processing carousel, decreasing in diameter. In some examples, the spiral track reaches the inner portion of the first carousel 102 after two rotations on the first carousel 102. The stat diverter may divert the reaction vessel from one section of the second track to another section of the second track, which causes the reaction vessel to bypass a portion of the second track and, in some examples, bypass a rotation on the first carousel 102. Thus, the stat diverter may be used to decrease the processing time of the reaction vessel. For example, if the reaction taking place in the reaction vessel requires a longer incubation time, then the reaction vessel continues on the second track (e.g., is not a stat reaction (block 926) and is not diverted) and is indexed Z6 positions (block 928). Z6 represents the number of positions around the track until a third divert location (e.g., a first wash zone) (block 934). In the example processing track 100 disclosed above, Z6 is the number of positions from the second diverter 124 to the third diverter 126 on the extended section of the second track 402. In some examples, Z6 may be 52.

Alternatively, if the reaction takes place at a faster rate, for example, the reaction is a stat reaction (block 926), and the reaction vessel is diverted (block 930) to another section of the second track and, thus, will be closer to the inner portion of the first carousel 102 and to the reader 130 and data gathering. In the example processing track 100 disclosed above, the second diverter 124 operates to divert a reaction vessel from one portion of the second track 402 to a different portion of the second track 402, bypassing an entire revolution on the second track before being analyzed by the reader 130.

If the reaction vessel is diverted (block 930), the example process 900 includes indexing the reaction vessel Z7 positions (block 932). In some examples, Z7 represents the number of positions from the second diverter to a third diverter location, where a first wash zone may be accessed. In the example processing track 100 disclosed above, Z7 is the number of positions from the second diverter 124 to the third diverter 126 on the shortened section of the second track 402. Therefore, in some examples, Z7 may be three.

The example process 900 includes a third diverter which includes determining whether a first wash is desired and/or needed (block 934). In some examples, the second track may include a third diverter to lead the reaction vessel to a first wash station where, for example, magnetic microparticle processing may occur and unwanted conjugate may be washed from the sample and magnetic microparticles. If a first wash is desired and/or needed (block 934), the reaction vessel is diverted to a side track of the second track that leads to the wash zone and the contents of the reaction vessel are washed (block 936). The example process 900 includes indexing the reaction vessel Z8 positions (block 936). Z8 represents the positions on the side track from the third diverter to a second reagent access point, discussed in detail below. In the example processing track 100 disclosed above, the third diverter 126 may divert a reaction vessel onto the wash zone side track 406 where the contents of the reaction vessel can be washed. In this example, Z8 may represent the locksteps or positions along the wash zone side track 406 from the third diverter 126 until the second reagent access point, e.g., point F. Therefore, in some examples, Z8 is set to 13.

If the reaction vessel is not diverted to the first wash zone (block 934), the example process includes indexing the reaction vessel Z9 positions on the processing carousel (block 940). In some examples, Z9 represents the number of positions along the second track from the wash zone diverter to a second reagent access or dispensation point. In the example processing track 100 shown above, the second track 402 splits at the third diverter 126 such that a reaction vessel may follow the wash zone side track 406 to be washed or may stay on the second track 402. In either path, the tracks reconnect before point F. Therefore, in some examples, Z9 is set to Z8.

The example process 900 in FIG. 9A continues in FIG. 9B. The example process 900 includes determining if a second reagent is to be added to the reaction vessel (block 940). In some examples, a second reagent pipette is disposed within the diameter of the processing carousel. In some examples, the second reagent pipette is to aspirate a second reagent and dispense the reagent into a reaction vessel. If it is determined that a second reagent is desired, the second reagent pipette dispenses a second reagent into the reaction vessel (block 944). In the example processing track 100 disclosed above, the third pipetting mechanism 234 is to aspirate a second reagent and dispense the second reagent into a reaction vessel on the first carousel 102 at point F.

In some examples, a second reagent is not to be added (block 942). The example process 900 includes indexing the reaction vessel Z10 positions (block 946). In some examples, Z10 represents the number of positions from the location at which the second reagent pipette is disposed or has access to the reaction vessels, to a location of a second wash zone. In the example processing track 100 disclosed above, a reaction vessel at point F on the first carousel 102 continues to index counterclockwise on the first carousel 102 into the second wash zone 136. In some examples, Z10 represents the number of locksteps, or index positions, between point F and the second wash zone 136. In some examples, Z10 is set to 16.

The example process 900 includes washing the contents of the reaction vessel (block 948). In some examples, the analytes of interests are attached to magnetic microparticles. Additional materials not of interest may also be attached to the magnetic microparticles. During the second wash step (block 948), any unwanted conjugate may be washed from the magnetic microparticles using, for example, magnetic microparticle processing.

The example process 900 includes indexing the reaction vessel Z11 positions (block 950). Z11 represents the number of positions between the second wash zone and a position where a reading is taken. In the example processing track 100 disclosed above, Z11 may represent the lockstep positions between the second wash zone 136 and the position of the reader 130.

The example process 900 includes reading the contents of the reaction vessel (block 952). In some examples, a reader is disposed along the processing carousel to analyze the contents of the reaction vessel. For example, during an example chemiluminescent reaction, the reader gathers photon data representative of a reaction and the contents of the reaction vessel.

The example process 900 also includes indexing the reaction vessel Z12 positions. In some examples, Z12 represents the number of index positions or locksteps until the reaction vessel is unloaded from the processing carousel. The example process 900 includes unloading the reaction vessel from its respective slot on the processing carousel (block 956). In some examples, a passive or active unloaded is disposed adjacent the processing carousel to remove vessels from the processing carousel. In the example processing track 100 disclosed above, the unloaded area 404 (FIG. 4A) represent an area where the reaction vessel may be unloaded. In the example shown, this is also the end of the second track 402. After unloading the reaction vessel from its slot on the processing carousel, the example process 900 ends (block 958) for that reaction vessel.

In some examples, the processing carousel continues to index and another reaction vessel may be added (block 902) to the same slot and another diagnostic analysis may take place using the sample process 900. Although only one reaction vessel was described in the process 900, multiple reaction vessels may be performing diagnostic analysis on a number of samples as the processing carousel rotates. In some examples, multiple reaction vessels may be disposed within the same slot on the process carousel. In such examples, a first reaction vessel may be engaged with the first track and be disposed in the outermost radial position in the slot, a second reaction vessel may be engaged with the second track and be disposed in the middle area of the slot, and a third reaction vessel may be disposed in the innermost radial position in the slot. Each of the reaction vessels may be at different stages of diagnostic testing.

Figure 10:
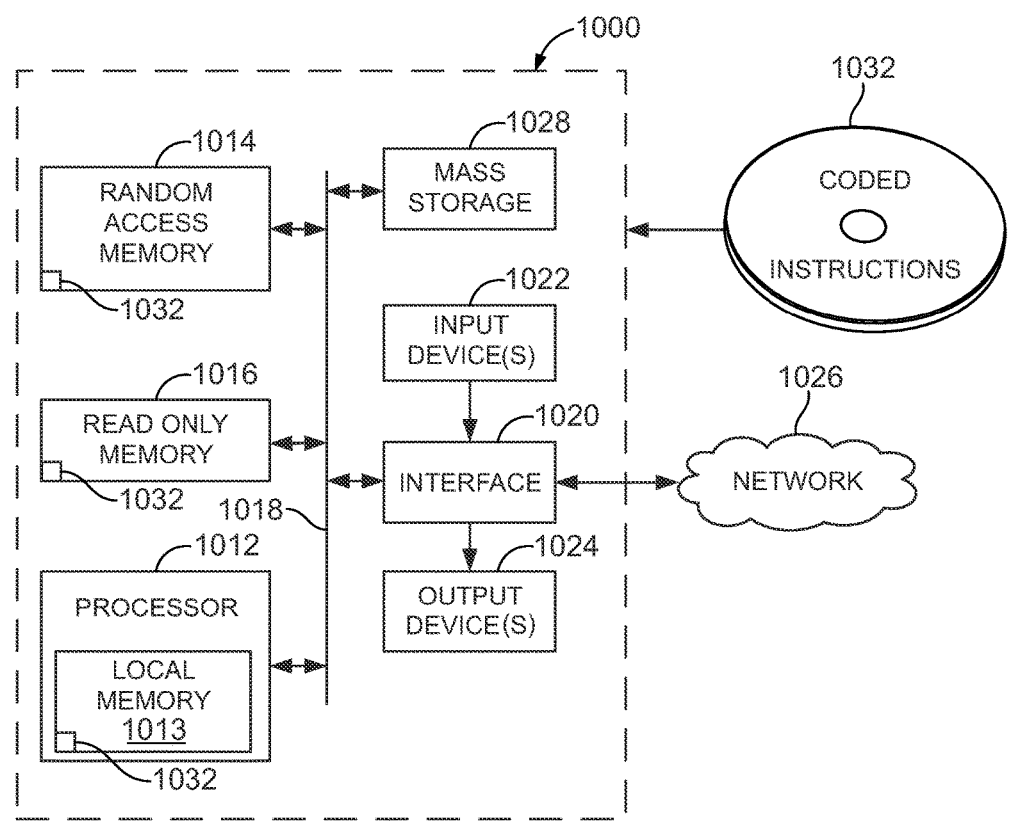
FIG. 10 is a diagram of a processor platform for use with the examples disclosed herein.

FIG. 10 is a block diagram of an example processor platform 1000 capable of executing the one or more instructions of FIGS. 7-9B to implement one or more portions of the apparatus and/or systems of FIGS. 1-6. The processor platform 1000 can be, for example, a server, a personal computer, a mobile device (e.g., a cell phone, a smart phone, a tablet such as an iPad™), a personal digital assistant (PDA), an Internet appliance, and/or or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors or controllers from any desired family or manufacturer.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 is controlled by a memory controller.

The processor platform 1000 of the illustrated example also includes an interface circuit 1020. The interface circuit 1020 may be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit(s) a user to enter data and commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device and/or a light emitting diode (LED). The interface circuit 1020 of the illustrated example, thus, typically includes a graphics driver card, a graphics driver chip or a graphics driver processor.

The interface circuit 1020 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1032 of FIGS. 7-9B may be stored in the mass storage device 1028, in the volatile memory 1014, in the non-volatile memory 1016, and/or on a removable tangible computer readable storage medium such as a CD or DVD.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An apparatus comprising:
   a first carousel comprising:

a first annular array of slots to receive a first reaction vessel;

a first track of rotation about the first carousel having a first diameter; and a second track of rotation about the first carousel having a second diameter smaller than the first diameter;

a first diverter to move the first reaction vessel from the first track to the second track;

a second carousel coaxial with the first carousel, the second carousel comprising a second annular array of slots to receive a second reaction vessel;

a vessel loader to load the first reaction vessel into one of the first annular array of slots and to load the second reaction vessel into one of the second annular array of slots;

a sample container having a liquid sample;

a first pipetting mechanism; and a computer processor including software programmed to control the first pipetting mechanism to aspirate an amount of the liquid sample from the sample container and dispense the amount of the liquid sample into the second reaction vessel on the second carousel.

2. The apparatus of claim 1, wherein the second carousel is concentric to the first carousel.

3. The apparatus of claim 1 further comprising a second diverter to move the first reaction vessel from a first portion of the second track to a second portion of the second track.

4. The apparatus of claim 3 further comprising a third diverter to move the first reaction vessel from the second track to a wash station.

5. The apparatus of claim 4 further comprising a fourth diverter to remove the second reaction vessel from the second carousel.

6. The apparatus of claim 1, wherein the first carousel comprises a first inner circumference and a first outer circumference, the second carousel comprises a second inner circumference and a second outer circumference, the second inner circumference is disposed outside of the first outer circumference.

7. The apparatus of claim 6, wherein the first pipetting mechanism is disposed outside of the second outer circumference.

8. The apparatus of claim 7, wherein the computer processor includes software programmed to control the first pipetting mechanism to aspirate from the second reaction vessel on the second carousel and to dispense to the first reaction vessel on the first carousel.

9. The apparatus of claim 7 further comprising a second pipetting mechanism disposed outside of the second outer circumference, the computer processor including software programmed to control the second pipetting mechanism to aspirate from a first reagent container disposed outside of the second outer circumference and to at least one of aspirate from or dispense to the second reaction vessel on the second carousel and to dispense to the first reaction vessel on the first carousel.

10. The apparatus of claim 9, wherein the first pipetting mechanism has a first pipette arm that is movable along a first path of travel over the first reaction vessel on the first carousel and the second reaction vessel on the second carousel during a stop of the first and second carousels, and the second pipetting mechanism has a second pipette arm that is movable along a second path of travel over a third reaction vessel on the first carousel and a fourth reaction vessel on the second carousel during the stop of the first and second carousels.

11. The apparatus of claim 10, wherein the first path of travel intersects the first carousel in two locations and the second carousel in two locations.

12. The apparatus of claim 9 further comprising a third pipetting mechanism disposed inside of the first inner circumference, the computer processor including software programmed to control the third pipetting mechanism to aspirate from a second reagent container disposed inside of the first inner circumference and to dispense into the first reaction vessel on the first carousel.

13. The apparatus of claim 12, wherein the third pipetting mechanism is offset from a first axis about which the first carousel and the second carousel are to rotate.

14. The apparatus of claim 12, wherein the computer processor includes software programmed to control the first pipetting mechanism to dispense to the first reaction vessel when the first reaction vessel is on the first track of the first carousel.

15. The apparatus of claim 14, wherein the computer processor includes software programmed to control the second pipetting mechanism to dispense to the first reaction vessel when the first reaction vessel is on the first track of the first carousel.

16. The apparatus of claim 15, wherein the computer processor includes software programmed to control the third pipetting mechanism to dispense to the first reaction vessel when the first reaction vessel is on the second track of the first carousel.

17. The apparatus of claim 12, wherein the computer processor includes software programmed to control the second pipetting mechanism to dispense a paramagnetic microparticle liquid into at least one of the first reaction vessel on the first carousel or the second reaction vessel on the second carousel.

18. The apparatus of claim 1, wherein each of the slots of the first annular array of slots is elongated to receive more than one reaction vessel.

19. The apparatus of claim 1, wherein a first slot of the first annular array of slots is to receive the first reaction vessel in the first track and a third reaction vessel in the second track.

20. The apparatus of claim 1, wherein the second annular array of slots comprises a greater number of slots than the first annular array of slots.

21. The apparatus of claim 1, wherein the second track comprises a spiral track, wherein the first reaction vessel in one of the first annular array of slots on the first carousel follows the spiral track as the first carousel rotates.

22. The apparatus of claim 21, wherein the spiral track decreases in diameter to lead the first reaction vessel from an outer radial location on the first carousel to an inner radial location on the first carousel.

23. The apparatus of claim 22, wherein the first reaction vessel in one of the first annular array of slots is to move from the outer radial location to the inner radial location after at least two rotations of the first carousel.

24. The apparatus of claim 1, wherein the computer processor includes software programmed to control the first carousel to rotate in a plurality of intervals, each interval comprising an advancement and a stop.

25. The apparatus of claim 24, wherein the computer processor includes software programmed to control the second carousel to rotate in a plurality of intervals, each interval comprising a major interval and a minor interval.

26. The apparatus of claim 25, wherein the minor interval of the second carousel comprises an advancement and a stop and the major interval of the second carousel comprises an advancement and a stop, the stop of the major interval being longer than the stop of the minor interval.

27. The apparatus of claim 1, wherein the apparatus is to perform an immunoassay.

28. The apparatus of claim 1, wherein the vessel loader is disposed over the first track of the first carousel and over the second carousel.

29. The apparatus of claim 1, wherein the vessel loader loads a plurality of empty reaction vessels into the first annular array of slots and the second annular array of slots.

30. The apparatus of claim 1, wherein the first reaction vessel and the second reaction vessel are a same type of reaction vessel.

31. The apparatus of claim 30, wherein the first reaction vessel and the second reaction vessel are open top vessels.

32. The apparatus of claim 1, wherein the first reaction vessel includes a first vessel body and a first rim extending outward from a top of the first vessel body, the first rim to support the first reaction vessel on the first carousel while the first vessel body extends through a first slot of the first annular array of slots in which the first reaction vessel is received.

33. The apparatus of claim 32, wherein the second reaction vessel includes a second vessel body and a second rim extending outward from a top of the second vessel body, the second rim to support the second reaction vessel on the second carousel while the second vessel body extends through a second slot of the second annular array of slots in which the second reaction vessel is received.

34. The apparatus of claim 33 further including a second diverter to remove the second reaction vessel from the second carousel.

35. The apparatus of claim 34, wherein the second diverter is disposed above the second carousel.

36. The apparatus of claim 34, wherein the second diverter is to rotate the second reaction vessel such that the second rim is not supported by the second carousel and falls through the second slot in the second carousel.

37. The apparatus of claim 1 further including a third carousel, the third carousel including a plurality of reagents.

38. The apparatus of claim 37, wherein the third carousel rotates about an axis that is offset from an axis about which the first and second carousels rotate.

39. The apparatus of claim 3, wherein moving the first reaction vessel from the first portion to the second portion of the second track results in the first reaction vessel bypassing one rotation about the second track.

40. The apparatus of claim 36 further including a passive unloader to unload the first reaction vessel from the first carousel.

41. The apparatus of claim 1, wherein the computer processor includes software programmed to:
control the second carousel to rotate the second reaction vessel while the amount of the liquid sample mixes with a reagent in the second reaction vessel; and
control the first pipetting mechanism to, after rotation of the second carousel, aspirate a mixture of the liquid sample and the reagent from the second reaction vessel and dispense the mixture into the first reaction vessel on the first carousel.

42. The apparatus of claim 1, further including a second pipetting mechanism, the computer processor including software programmed to control the second pipetting mechanism to:
dispense a reagent into the second reaction vessel;
aspirate a mixture of the liquid sample and the reagent from the second reaction vessel; and
dispense the mixture into the first reaction vessel on the first carousel.

43. The apparatus of claim 1, wherein the first annular array of slots includes a first plurality of slots having a first width, and the second annular array of slots includes a second plurality of slot having the first width.

44. The apparatus of claim 43, wherein the first plurality of slots have a first length, and the second plurality of slots have a second length, the second length shorter than the first length.

45. The apparatus of claim 1, wherein the first carousel has a first support surface, and the second carousel has a second support surface, the second support surface co-planar with the first support surface.

* * * * *